US009777278B2

(12) United States Patent
Liang et al.

(10) Patent No.: US 9,777,278 B2
(45) Date of Patent: Oct. 3, 2017

(54) LONG INTERFERING NUCLEIC ACID DUPLEXES TARGETING MULTIPLE RNA TARGETS

(71) Applicant: Biomics Biotechnologies Co., Ltd., Nantong (CN)

(72) Inventors: Dong Liang, Everett, WA (US); David Sweedler, Louisville, CO (US); Kunyuan Cui, Botthell, WA (US)

(73) Assignee: BIOMICS BIOTECHNOLOGIES CO., LTD, Nantong (CN)

( * ) Notice: Subject to any disclaimer, the term of this patent is extended or adjusted under 35 U.S.C. 154(b) by 0 days.

(21) Appl. No.: 14/826,818

(22) Filed: Aug. 14, 2015

(65) Prior Publication Data
US 2016/0040170 A1 Feb. 11, 2016

Related U.S. Application Data

(63) Continuation of application No. 12/231,900, filed on Sep. 5, 2008, now abandoned.

(60) Provisional application No. 61/069,029, filed on Mar. 13, 2008, provisional application No. 61/065,844, filed on Feb. 16, 2008, provisional application No. 60/992,695, filed on Dec. 5, 2007, provisional application No. 60/969,951, filed on Sep. 5, 2007.

(51) Int. Cl.
| | |
|---|---|
| *C07H 21/02* | (2006.01) |
| *C07H 21/04* | (2006.01) |
| *A61K 48/00* | (2006.01) |
| *C12N 15/113* | (2010.01) |
| *C12N 15/11* | (2006.01) |

(52) U.S. Cl.
CPC ........ *C12N 15/1138* (2013.01); *C12N 15/111* (2013.01); *C12N 15/1136* (2013.01); *C12N 2310/14* (2013.01); *C12N 2310/141* (2013.01); *C12N 2310/341* (2013.01); *C12N 2310/351* (2013.01); *C12N 2310/51* (2013.01); *C12N 2310/53* (2013.01); *C12N 2310/531* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 7,517,864 B2 | 4/2009 | Vargeese et al. | |
| 2004/0224405 A1 | 11/2004 | Leake et al. | |
| 2006/0009409 A1* | 1/2006 | Woolf | A61K 31/713 514/44 A |
| 2006/0211637 A1* | 9/2006 | Scaria | A61K 48/00 514/44 A |
| 2006/0281702 A1* | 12/2006 | Gorenstein | C12N 15/111 514/44 A |
| 2007/0032441 A1 | 2/2007 | McSwiggen et al. | |
| 2008/0242632 A1* | 10/2008 | Rossi | C12N 15/111 514/44 A |
| 2009/0182136 A1* | 7/2009 | Wengel | C12N 15/111 536/24.5 |
| 2010/0022618 A1 | 1/2010 | Liang et al. | |
| 2014/0134619 A1* | 5/2014 | Jenison | C12Q 1/6844 435/6.11 |

FOREIGN PATENT DOCUMENTS

WO 2007056826 5/2007

OTHER PUBLICATIONS

Paddison et al. (Genes & Dev. 16: 948-958, 2002).*
Dogan et al. 5'-Tethered Stilbene as Fidelity- and Affinity-Enhancing Modulators of DNA Duplex Stability, J. Am. Chem. Soc., 2004, vol. 126, Issue 15, p. 4762-4763.
Mahato et al., Modulation of gene expression by antisense and antigene oligodeoxynucleotides and small interfering RNA, Jan. 2005, Expert Opinion on Drug Delivery, vol. 2, No. 1, pp. 3-28.
Scherer et al., Approaches for the sequence-specific knockdown of mRNA, 2003, Nat. Biotechnol., 21 (12), pp. 1457-1465.
International Search Report corresponding to International Application No. PCT/US2008/010423, dated Mar. 9, 2009.
International Preliminary Report on Patentability corresponding to International Application No. PCT/US2008/010423, dated Jun. 14, 2011.
Written Opinion of the International Searching Authority corresponding to International Application No. PCT/US2008/010423, dated Mar. 9, 2009.

* cited by examiner

*Primary Examiner* — Amy Bowman
(74) *Attorney, Agent, or Firm* — K&L Gates LLP; Louis C. Cullman; David Diamond

(57) ABSTRACT

Long interfering nucleic acid (iNA) duplexes, which are at least 30 nucleotides in length, which have at least one nick or nucleotide gap in the antisense or the sense strands or in both the sense and antisense strands. These long iNA duplexes do not induce an interferon response when transfected into mammalian cells. The antisense strands can target two separate mRNAs or two segments of one mRNA.

23 Claims, 18 Drawing Sheets

Interferon responses with 40 mer siRNA variants

SiRNA activity in inhibition of LAC Z enzyme expression with designed siRNAs

SEQUENCE LISTING

```
<160> NUMBER OF SEQ ID NOS: 41

<210> SEQ ID NO 1
<211> LENGTH: 45
<212> TYPE: DNA
<213> ORGANISM: Homo sapiens

<400> SEQUENCE: 1
uucuacauca cugagggact tcucauuuac acgucugcgg aucuu              45

<210> SEQ ID NO 2
<211> LENGTH: 21
<212> TYPE: DNA
<213> ORGANISM: Homo sapiens

<400> SEQUENCE: 2
gucccucagu gauguagaat t                                        21

<210> SEQ ID NO 3
<211> LENGTH: 45
<212> TYPE: DNA
<213> ORGANISM: Homo sapiens

<400> SEQUENCE: 3
uguugcuccu ucuuucaaca tuuuuuugca ggaacauuua cacgu              45

<210> SEQ ID NO 4
<211> LENGTH: 45
<212> TYPE: RNA
<213> ORGANISM: Homo sapiens
```

-continued

<400> SEQUENCE: 4
uucuacauca cugagggacu ucucauuuac acgucugcgg aucuu                            45

<210> SEQ ID NO 5
<211> LENGTH: 21
<212> TYPE: DNA
<213> ORGANISM: Homo sapiens

<400> SEQUENCE: 5
gucccucagu gauguagaat t                                                     21

<210> SEQ ID NO 6
<211> LENGTH: 21
<212> TYPE: RNA
<213> ORGANISM: Homo sapiens

<400> SEQUENCE: 6
aagauccgca gacguguaaa u                                                     21

<210> SEQ ID NO 7
<211> LENGTH: 45
<212> TYPE: DNA
<213> ORGANISM: Homo sapiens

<400> SEQUENCE: 7
uguugcuccu ucuuucaaca tuuuuuugca ggaacauuua cacgu                            45

<210> SEQ ID NO 8
<211> LENGTH: 21
<212> TYPE: DNA
<213> ORGANISM: Homo sapiens

<400> SEQUENCE: 8
gucccucagu gauguagaat t                                                     21

<210> SEQ ID NO 9
<211> LENGTH: 21
<212> TYPE: RNA
<213> ORGANISM: Homo sapiens

<400> SEQUENCE: 9
acguguaaau guuccugcaa a                                                     21

<210> SEQ ID NO 10
<211> LENGTH: 45
<212> TYPE: DNA
<213> ORGANISM: Homo sapiens

<400> SEQUENCE: 10
uucaaauguu uuuacacuca cagcacaucu gcaaguacgu ucguu                            45

<210> SEQ ID NO 11
<211> LENGTH: 21
<212> TYPE: DNA
<213> ORGANISM: Homo sapiens

<400> SEQUENCE: 11
gaguguaaaa acauuugaat t                                                     21

<210> SEQ ID NO 12
<211> LENGTH: 21
<212> TYPE: RNA

-continued

<213> ORGANISM: Homo sapiens

<400> SEQUENCE: 12
aacgaacgua cuugcagaug u                                    21

<210> SEQ ID NO 13
<211> LENGTH: 20
<212> TYPE: DNA
<213> ORGANISM: Homo sapiens

<400> SEQUENCE: 13
acaucugcaa guacguucgt                                      20

<210> SEQ ID NO 14
<211> LENGTH: 21
<212> TYPE: DNA
<213> ORGANISM: Homo sapiens

<400> SEQUENCE: 14
auuuacacgu cugcggauct t                                    21

<210> SEQ ID NO 15
<211> LENGTH: 21
<212> TYPE: DNA
<213> ORGANISM: Homo sapiens

<400> SEQUENCE: 15
guguaaaugu uccugcaaat t                                    21

<210> SEQ ID NO 16
<211> LENGTH: 21
<212> TYPE: DNA
<213> ORGANISM: Homo sapiens

<400> SEQUENCE: 16
uuugcaggaa cauuuacacg t                                    21

<210> SEQ ID NO 17
<211> LENGTH: 43
<212> TYPE: DNA
<213> ORGANISM: Homo sapiens

<400> SEQUENCE: 17
gauccgcaga cguguaaaut tugugagugu aaaaacauuu gaa            43

<210> SEQ ID NO 18
<211> LENGTH: 45
<212> TYPE: DNA
<213> ORGANISM: Homo sapiens

<400> SEQUENCE: 18
uucuacauca cugagggact tcucauuuac acgucugcgg aucuu          45

<210> SEQ ID NO 19
<211> LENGTH: 45
<212> TYPE: DNA
<213> ORGANISM: Homo sapiens

<400> SEQUENCE: 19
uguugcuccu ucuuucaaca tuuuuuugca ggaacauuua cacgu          45

<210> SEQ ID NO 20
<211> LENGTH: 21

```
<212> TYPE: DNA
<213> ORGANISM: Homo sapiens

<400> SEQUENCE: 20
uguugcuccu ucuuucaaca t                                          21

<210> SEQ ID NO 21
<211> LENGTH: 21
<212> TYPE: DNA
<213> ORGANISM: Homo sapiens

<400> SEQUENCE: 21
gaguguaaaa acauuugaat t                                          21

<210> SEQ ID NO 22
<211> LENGTH: 21
<212> TYPE: RNA
<213> ORGANISM: Homo sapiens

<400> SEQUENCE: 22
uucaaauguu uuuacacuca c                                          21

<210> SEQ ID NO 23
<211> LENGTH: 21
<212> TYPE: DNA
<213> ORGANISM: Homo sapiens

<400> SEQUENCE: 23
gucccucagu gauguagaat t                                          21

<210> SEQ ID NO 24
<211> LENGTH: 21
<212> TYPE: DNA
<213> ORGANISM: Homo sapiens

<400> SEQUENCE: 24
uucuacauca cugagggact t                                          21

<210> SEQ ID NO 25
<211> LENGTH: 21
<212> TYPE: DNA
<213> ORGANISM: Homo sapiens

<400> SEQUENCE: 25
tttgacatcc ctgaggagat t                                          21

<210> SEQ ID NO 26
<211> LENGTH: 22
<212> TYPE: DNA
<213> ORGANISM: Homo sapiens

<400> SEQUENCE: 26
gatagacatt agccaggagg tt                                         22

<210> SEQ ID NO 27
<211> LENGTH: 20
<212> TYPE: DNA
<213> ORGANISM: Homo sapiens

<400> SEQUENCE: 27
gtgagctcct ggattctgct                                            20

<210> SEQ ID NO 28
```

<211> LENGTH: 25
<212> TYPE: DNA
<213> ORGANISM: Homo sapiens

<400> SEQUENCE: 28
tgttccaatg taaccatatt tctga					25

<210> SEQ ID NO 29
<211> LENGTH: 45
<212> TYPE: DNA
<213> ORGANISM: Homo sapiens

<400> SEQUENCE: 29
gauccgcaga cguguaaaut tugugagugu aaaaacauuu gaatt				45

<210> SEQ ID NO 30
<211> LENGTH: 43
<212> TYPE: DNA
<213> ORGANISM: Homo sapiens

<400> SEQUENCE: 30
gauccgcaga cguguaaaut tugugagugu aaaaacauuu gaa				43

<210> SEQ ID NO 31
<211> LENGTH: 45
<212> TYPE: DNA
<213> ORGANISM: Homo sapiens

<400> SEQUENCE: 31
uucuacauca cugagggact tcucauuuac acgucugcgg aucuu				45

<210> SEQ ID NO 32
<211> LENGTH: 45
<212> TYPE: RNA
<213> ORGANISM: Homo sapiens

<400> SEQUENCE: 32
uucuacauca cugagggacu ucucauuuac acgucugcgg aucuu				45

<210> SEQ ID NO 33
<211> LENGTH: 45
<212> TYPE: DNA
<213> ORGANISM: Homo sapiens

<400> SEQUENCE: 33
uguugcuccu ucuuucaaca tuuuuuugca ggaacauuua cacgu				45

<210> SEQ ID NO 34
<211> LENGTH: 45
<212> TYPE: RNA
<213> ORGANISM: Homo sapiens

<400> SEQUENCE: 34 uucaauguu uuuacacuca cagcacaucu gcaaguacgu ucguu				45

<210> SEQ ID NO 35
<211> LENGTH: 45
<212> TYPE: DNA
<213> ORGANISM: Homo sapiens

<400> SEQUENCE: 35
gauccgcaga cguguaaaut tugugagugu aaaaacauuu gaatt				45

```
<210> SEQ ID NO 36
<211> LENGTH: 44
<212> TYPE: DNA
<213> ORGANISM: Homo sapiens

<400> SEQUENCE: 36
gauccgcaga cguguaaaut tcugugagug uaaaaacauu ugaa            44

<210> SEQ ID NO 37
<211> LENGTH: 67
<212> TYPE: DNA
<213> ORGANISM: Homo sapiens

<400> SEQUENCE: 37
gauccgcaga cguguaaaut tugugagugu aaaaacauuu gaattacgag aucuaugaga    60
ucaugca                                                             67

<210> SEQ ID NO 38
<211> LENGTH: 21
<212> TYPE: RNA
<213> ORGANISM: Homo sapiens

<400> SEQUENCE: 38
ugcaugaucu cauagaucuc g                                     21

<210> SEQ ID NO 39
<211> LENGTH: 35
<212> TYPE: DNA
<213> ORGANISM: Escherichia coli

<400> SEQUENCE: 39
ucagcgauuu gagaaaaucg cugauuugug uagtc                      35

<210> SEQ ID NO 40
<211> LENGTH: 44
<212> TYPE: RNA
<213> ORGANISM: Escherichia coli

<400> SEQUENCE: 40
gcgauuucca ugugagaaca uggaaaucgc ugauuugugu aguc            44

<210> SEQ ID NO 41
<211> LENGTH: 12
<212> TYPE: RNA
<213> ORGANISM: Escherichia coli

<400> SEQUENCE: 41
cuacacaaau ca                                               12
```

LONG INTERFERING NUCLEIC ACID DUPLEXES TARGETING MULTIPLE RNA TARGETS

CROSS REFERENCE TO RELATED APPLICATIONS

This claims is a continuation of U.S. patent application Ser. No. 12/231,900 filed Sep. 5, 2008, which claims priority under 35 U.S.C. §119 (e) of U.S. Provisional Application 61/069,029 filed Mar. 13, 2008; U.S. Provisional Application 61/065,844 filed Feb. 16, 2008; U.S. Provisional Application 60/992,695 filed Dec. 5, 2007; and U.S. Provisional Application 60/969,951 filed Sep. 5, 2007, all the teachings of which are incorporated in their entirety herein by reference.

BACKGROUND

All publications, references, patents, patent publications and patent applications cited herein are each hereby specifically incorporated by reference in its entirety.

RNA interference (RNAi) is a form of post-transcriptional gene silencing in which double-stranded RNA (dsRNA) induces the enzymatic degradation of homologous messenger RNA (mRNA). When a long dsRNA enters a cell, an enzyme called Dicer binds and cleaves long, dsRNA. Cleavage by Dicer results in the production of a small interfering RNA (iRNA) that is generally 20-25 base pairs in length and has a 2-nucleotide-long 3' overhang on each strand. Generically, an interfering RNA is also called an interfering nucleic acid (iNA), because non-RNA nucleotides can be incorporated into the construct. One of the two strands of each iNA, generally the antisense strand, is then incorporated into an RNA-induced silencing complex (RISC), and pairs with complementary sequences. RISC first mediates the unwinding of the iNA duplex. A single-stranded iNA that is coupled to RISC, then binds to a target mRNA in a sequence-specific manner. The binding mediates target mRNA cleavage by Slicer, an argonaute protein that is the catalytic component of RISC. The cleavage of the mRNA prevents translation from occurring, which prevents the ultimate expression of the gene from which the mRNA was transcribed.

As the fragments produced by Dicer are double-stranded, they could each in theory produce a functional iNA. The strand selected to be that with a less stable 5' end.

RNA interference has a tremendous potential in medicinal therapeutics, such as in anti-viral, oncogenic and anti-inflammatory applications. The double-stranded iNA may be a long double-strand designed to be cleaved by Dicer, called Dicer substrate. Or the iNA may be short and designed to bypass Dicer serve directly as a RISC substrate. The dsRNAs are synthesized with a sequence complementary to a gene of interest and introduced into a cell or organism, where it is recognized as exogenous genetic material and activates the RNAi pathway. Using this mechanism, RNA interference can cause a drastic decrease in the expression of a targeted gene.

Medicine

RNAi interference can be used to develop a whole new class of therapeutics. Although it is difficult to introduce long dsRNA strands into mammalian cells due to the interferon response, the use of short interfering RNA mimics has been more successful. Among the first applications to reach clinical trials were in the treatment of age-related macular degeneration, and respiratory syncytial virus. Other proposed clinical uses center on antiviral therapies, including the inhibition of viral gene expression in cancerous cells, knockdown of host receptors and co-receptors for HIV, the silencing of hepatitis A, hepatitis B and hepatitis C genes, silencing of influenza gene expression, and inhibition of measles viral replication. Potential treatments for neurodegenerative diseases have also been proposed, with particular attention being paid to the polyglutamine diseases such as Huntington's disease. RNA interference is also often seen as a promising way to treat cancer by silencing genes differentially up-regulated in tumor cells or genes involved in cell division. A key area of research in the use of RNAi for clinical applications is the development of a safe delivery method, which to date has involved mainly viral vector systems similar to those suggested for gene therapy.

Despite the proliferation of promising cell culture studies for RNAi-based drugs, some concern has been raised regarding the safety of RNA interference, especially the potential for "off-target" effects in which a gene with a coincidentally similar sequence to the targeted gene is also repressed. A computational genomics study estimated that the error rate of off-target interactions is about 10%. In mammalian cells, however, the use of RNAi for targeted gene silencing has been limited due to nonspecific effects induced by long dsRNAs, which result in interferon response. Therefore, for applications in mammals, iNAs had to be designed to be less than 30 based pairs in length to prevent the PKR response.

However, in developing a therapeutic drug for a mammal, it would be desirable to create a long iNA for use in RNAi. An example of this is an iNA that contains multiple therapeutic targets, such as a sequence that anneals to an mRNA that produces a ligand and a sequence that anneals to the mRNA that produces the receptor of the ligand. However, such a long dsRNA containing two targets would induce the interferon response resulting in undesirable side effects to the patient.

Thus, there is a need to produce iNAs that can target more than one mRNA or more than one target or subsequence on a single mRNA.

DESCRIPTION

The disclosed compounds and processes fill this need by providing for interfering nucleic acid (iNA) duplexes having antisense sequences that can target or hybridize to two or more mRNAs or two or more microRNA (miRNA) or two or more subsequences of one mRNA or miRNA and which does not induce an interferon response. The present invention further provides for an iNA having a discontinuous antisense strand and an intact sense strand. In an alternative embodiment, the sense strand can be discontinuous and the antisense strand is intact and the antisense strand can target two different mRNAs or two different sequences on a single mRNA. Generally, the iNA is comprised of a sense strand and an antisense strand in which the total length of the duplex is at least 30 nucleotides in length and one or both of the strands of the iNA duplex has a nick or a gap in the nucleotide strand. This results in the segmentation of the sense or antisense strands. The use of such a long iNA having a segmented sense or antisense strand unexpectedly results in the lowering of an interferon response in a mammalian cell that would be predicted when a double-stranded RNA that has a length of at least 30 nucleotides is introduced into the cytoplasm of a mammalian cell.

The present invention further provides for an interfering nucleic acid (iNA) duplex comprised of a sense strand of nucleotides having a 5' end and a 3' end annealed onto an antisense strand of nucleotides having a 5' end and a 3' end wherein the antisense strand has at least two segments, wherein one segment of the antisense strand can target a first RNA and another segment of the antisense strand can target a second RNA, or one segment of the antisense strand can is a target to a first portion of an RNA and another segment of the antisense strand is target to a second portion of said RNA, and wherein the iNA does not induce an interferon-response when transfected into a cell.

The present invention further provides for an iNA duplex comprised of a sense strand of nucleotides, and two or more antisense strands annealed to the sense strand wherein there is at least one nucleotide gap or a nick between the antisense strands, and wherein the iNA duplex has a length of at least 30 nucleotides, and wherein each antisense strand a has 5' and a 3' end and the sense strand has a 5' end and a 3' end.

The disclosed compounds and processes further fill this need by providing for interfering nucleic acid (iNA) duplexes comprised of a sense strand and an antisense strand in which one or both of the strands of the iNA duplex has at least one nick or at least one nucleotide gap in the nucleotide strand resulting in the segmentation of the sense or antisense strands such that there are two or more partial sense strands or two or more partial antisense strands and at least one of the partial sense strand or partial antisense strand has a molecular cap attached to at least one nucleotide of the strand. For example, at the 5' end or 3' end of at least one of the partial sense strands or partial antisense strands is a molecular cap covalently bonded to the nucleotide at a 5' or a 3' end of a partial sense or a partial antisense strand.

The present invention further provides for an iNA duplex comprised of a sense strand and an antisense strand, wherein the antisense strand is annealed to the sense strand, wherein there is at least one nick or one nucleotide gap in the antisense strand, and wherein the iNA duplex has a length of at least 30-80 nucleotides and wherein there is at least one nick or at least one nucleotide gap in the sense strand.

The present invention further provides for an iNA duplex comprised of two or more sense strands and two or more antisense strands wherein the antisense strands are annealed to the sense strands so as to produce one iNA duplex, and wherein said iNA duplex has a length of at least 30-80 nucleotides.

The present invention further provides for a pharmaceutical composition comprised of an iNA duplex having a sense strand of nucleotides having a 5' end and a 3' end annealed onto two or more antisense strands of nucleotides each strand having a 5' end and a 3' end wherein one antisense strand can target a first mRNA and one antisense strand can target a second mRNA, or one antisense strand can target one site on an mRNA and one antisense strand can target another site on said mRNA and wherein the iNA does not induce an interferon-response when transfected into a cell, and a pharmaceutically acceptable excipient.

The present invention further provides for a method for down-regulating an mRNA in a mammal comprising administering an iNA to said mammal wherein said iNA duplex has a sense strand of nucleotides having a 5' end and a 3' end annealed onto two or more antisense strands of nucleotides each strand having a 5' end and a 3' end wherein one antisense strand can target a first segment of said mRNA and a second antisense strand can target a second segment of said mRNA, and wherein the iNA does not induce an interferon-response when transfected into a cell.

The present invention further provides for an iNA duplex comprised of two or more sense strands and two or more antisense strands wherein the antisense strands are annealed to the sense strands so as to produce one iNA duplex, wherein each of the antisense strands target different mRNAs or different sites on one mRNA or different miRNAs and at least one sense strand that can target an mRNA or miRNA and wherein said iNA duplex has a length of at least 30-80 nucleotides.

The disclosed capped iNA constructs can be designed to take advantage of the observations that the thermodynamically least stable 5' end of an iNA construct is preferentially utilized at the antisense strand in activated RISC. The chemical structures of the preferred caps are shown in FIG. 14. Compound A in FIG. 14 is pyrenylmethylpyrrolindol and compound B in FIG. 14 is trimethoxystilbene. Pyrenylmethylpyrrolindol produces a cap that is more lipophilic than the cap produced by trimethoxystilbene. Both of these compounds are phosphoramadites that can be readily introduced by automated nucleic acid synthesis. The preferred 5' caps shown in FIG. 14 are described by Narayanan et al., Nucleic Acid Res. 32:2901-2911 (2004) and sold by Glen Research, Sterling, Va.

Preferably each partial sense or antisense strand should be at least 9 nucleotides long to properly anneal to its complementary antisense or sense sequence. If it is desired that a particular partial strand be an available target to an mRNA, then the length of the partial sequence should be at least 14 nucleotides in length or more in length.

This disclosure provides for pharmaceutically acceptable nucleic acid compositions useful for therapeutic delivery of nucleic acids and gene-silencing iNAs. In particular, this invention provides compositions and methods for in vitro and in vivo delivery of iNAs applicable for decreasing, down regulating, or silencing the translation of a target nucleic acid sequence or expression of a gene. These compositions and methods may be used for prevention and/or treatment of diseases in a mammal. A therapeutic strategy based on RNAi can be used to treat a wide range of diseases by shutting down the growth or function of a virus or microorganism, as well as by shutting down the function of an endogenous gene product in the pathway of the disease.

In some embodiments, this invention provides novel compositions and methods for delivery of RNAi-inducing entities such as long interfering oligonucleotide molecules having one or more segmented or partial strands wherein one or more of the segmented strands is capped by a molecular cap covalently bonded at the 5' or 3' end of the partial nucleic acid strand. In particular, this invention further provides for compositions containing an RNAi-inducing entity that is targeted to one or more transcripts of a cell, tissue, and/or organ of a subject.

The iNAs can mediate selective gene silencing in the mammalian system. Hairpin iNAs, with a short loop and a stem that has a nick or nucleotide gap in the sense or antisense strands and a cap at the 5' or 3' end of a segmented strand also selectively silence expression of genes that are homologous to a sequence in the double-stranded stem. Mammalian cells can convert hairpin iNA into iNA to mediate selective gene silencing.

Preferably each partial sense or antisense strand should be at least 9 nucleotides long to properly anneal to its complementary antisense or sense sequence. If it is desired that a particular partial strand be available as a target to an mRNA, then the length of the partial sequence should be at least 14 nucleotides in length, preferably 17-27 nucleotides or more in length.

It has been surprisingly discovered that when such an iNA duplex having a length of at least 30 nucleotides and a segmented sense or antisense strand, is transfected into a mammalian cell, the expected interferon response is greatly reduced or undetectable. This allows for the use of iNA duplexes that are 30-80 or more nucleotides in length.

This disclosure provides pharmaceutically acceptable nucleic acid compositions useful for therapeutic delivery of nucleic acids and gene-silencing iNAs. In particular, this invention provides compositions and methods for in vitro and in vivo delivery of iNAs decreasing, down-regulating, or silencing the translation of a target nucleic acid sequence or expression of a gene. These compositions and methods may be used for prevention and/or treatment of diseases in a mammal. A therapeutic strategy based on RNAi can be used to treat a wide range of diseases by shutting down the growth or function of a virus or microorganism, as well as by shutting down the function of an endogenous gene product in the pathway of the disease.

In some embodiments, this invention provides novel compositions and methods for delivery of RNAi-inducing entities such as long interfering oligonucleotide molecules having one or more segmented strands, and precursors thereof. In particular, this invention further provides for compositions containing an RNAi-inducing entity that is targeted to one or more transcripts of a cell, tissue, and/or organ of a subject.

The iNAs can mediate selective gene silencing in the mammalian system. Hairpin iNAs, with a short loop and a stem that has a length of at least 30 nucleotides and has a nick or nucleotide gap in the sense or antisense strands also selectively silence expression of genes that are homologous to a sequence in the double-stranded stem. Mammalian cells can convert hairpin iNA into iNA to mediate selective gene silencing.

By having the ability to transfect a mammalian cell with an iNA duplex that is 30 nucleotides in length or longer, one can design iNA duplexes that have an antisense strand that can be processed to target more than one mRNA. For example, one segment of the antisense strand could target the mRNA for a ligand while a second segment of the same antisense strand could target the mRNA of a receptor or another ligand. Each segment should be at least 16, 17, 18, 19, 20 or 21 nucleotides in length or longer, thus the length of each iNA duplex will be preferably 32 to 80 nucleotides in length or longer. In another embodiment, both the sense and antisense strands can be designed so that one or more segments of both the sense and antisense strands target one or more mRNAs.

The iNAs can be delivered as single or multiple transcription products expressed by a polynucleotide vector encoding the single or multiple iNAs and directing their expression within target cells. Typically, the iNA will target a gene that is expressed at an elevated level as a causal or contributing factor associated with the subject disease state or adverse condition. In this context, the iNA will effectively down-regulate expression of the gene to levels that prevent, alleviate, or reduce the severity or recurrence of one or more associated disease symptoms. Alternatively, for various distinct disease models where expression of the target gene is not necessarily elevated as a consequence or sequel of disease or other adverse condition, down-regulation of the target gene will nonetheless result in a therapeutic result by lowering gene expression (i.e., to reduce levels of a selected mRNA and/or protein product of the target gene). Alternatively, iNAs of the invention may be targeted to lower expression of one gene, which can result in upregulation of a "downstream", gene whose expression is negatively regulated by a product or activity of the target gene.

DEFINITION

Figure 1:
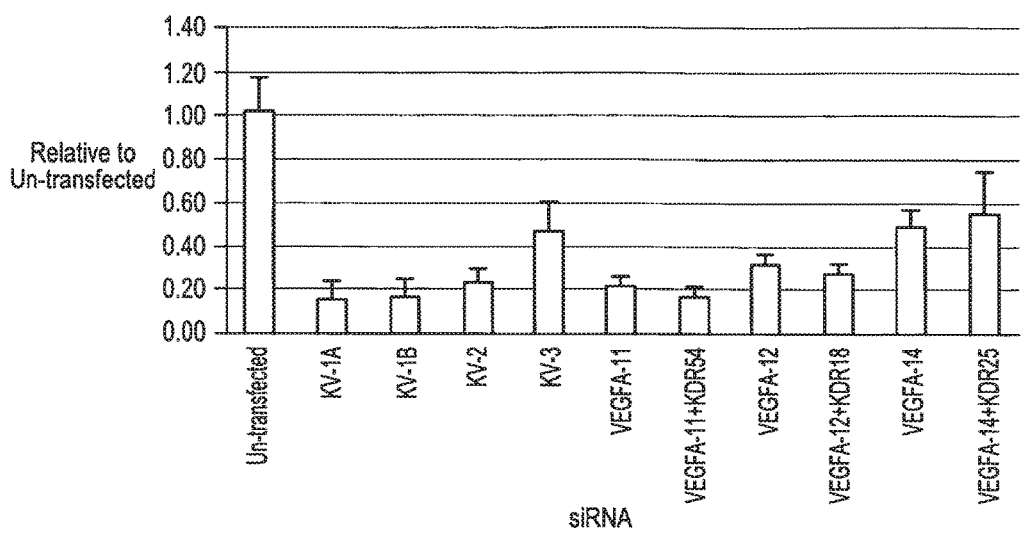
FIG. 1 shows the ability of iNA constructs disclosed in the specification to inhibit the expression of VEGF.
Figure 2:
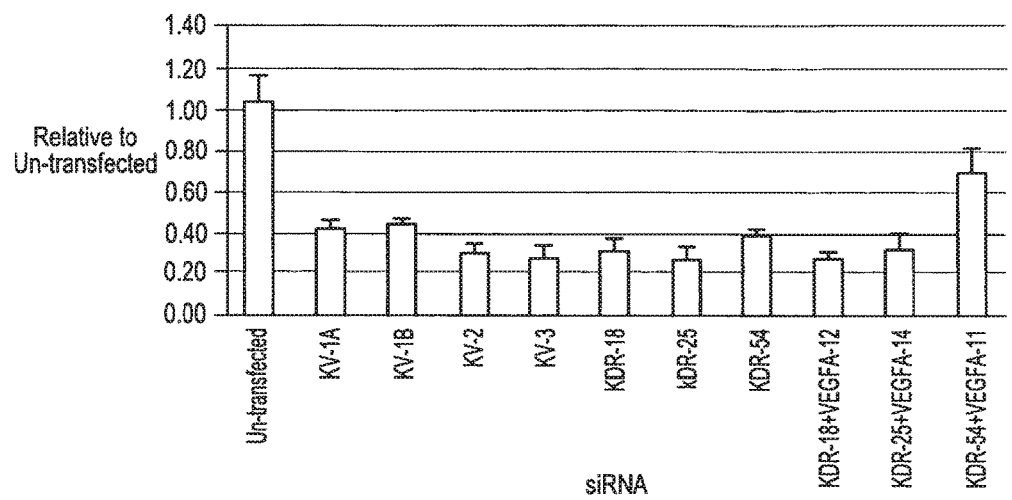
FIG. 2 shows the ability of iNA constructs disclosed in the specification to inhibit the expression of KDR.
Figure 3:
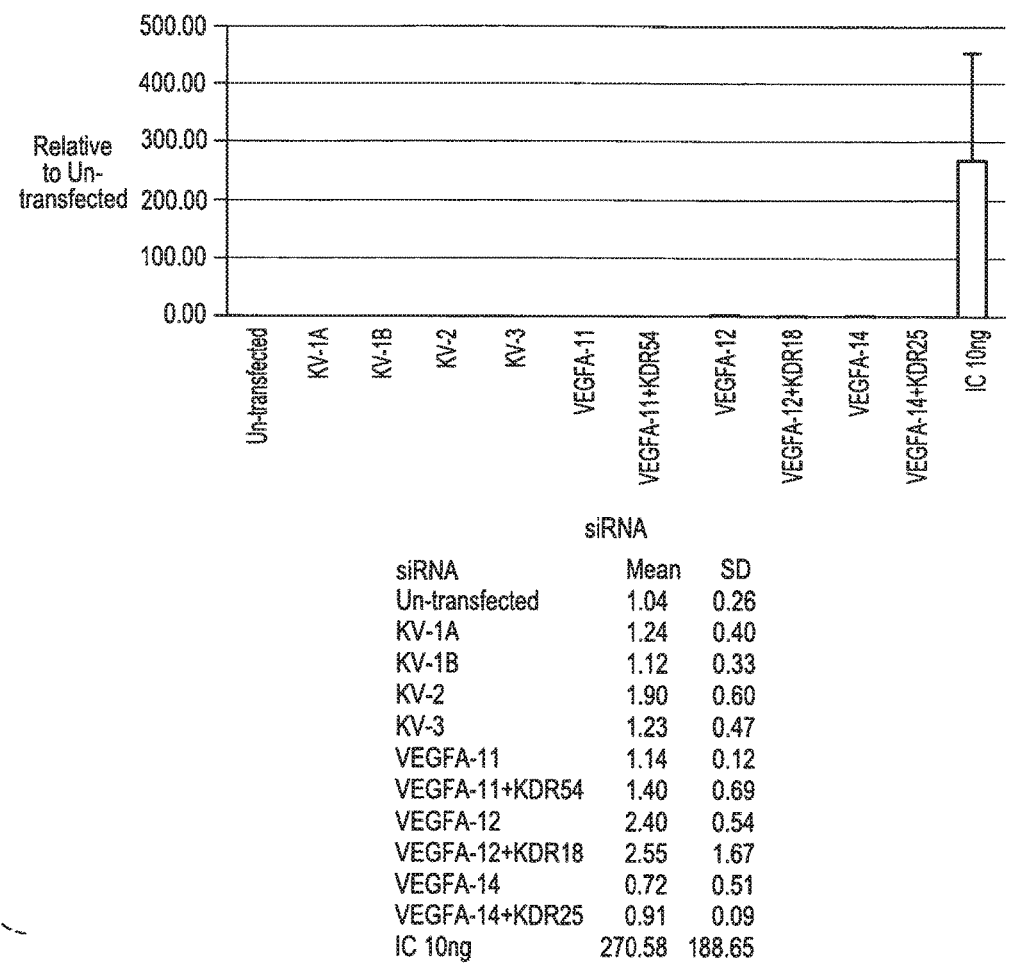
FIG. 3 shows the level of interferonβ1 (IFNβ1) induced when iNA constructs disclosed in the specification are transfected into ARPE-19 cells.
Figure 4:
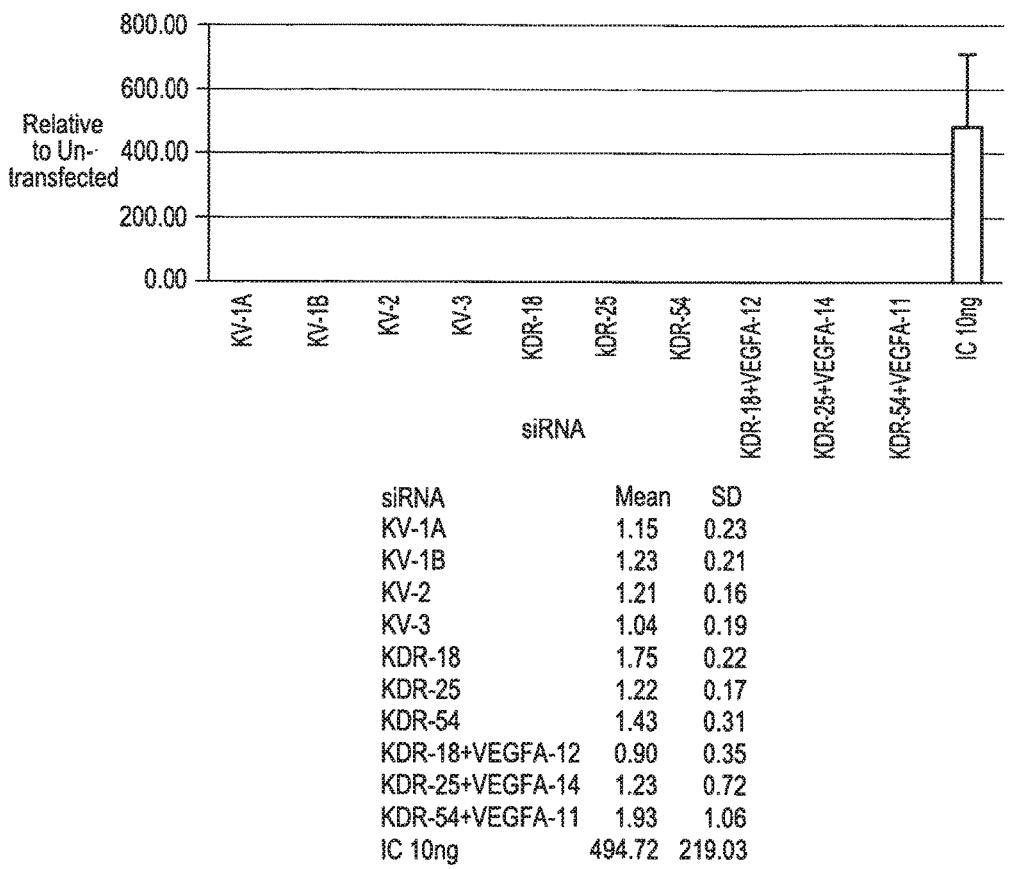
FIG. 4 shows the level of interferonβ1 (IFNβ1) induced when iNA constructs disclosed in the specification are transfected into HUVEC-CS cells.
Figure 5:
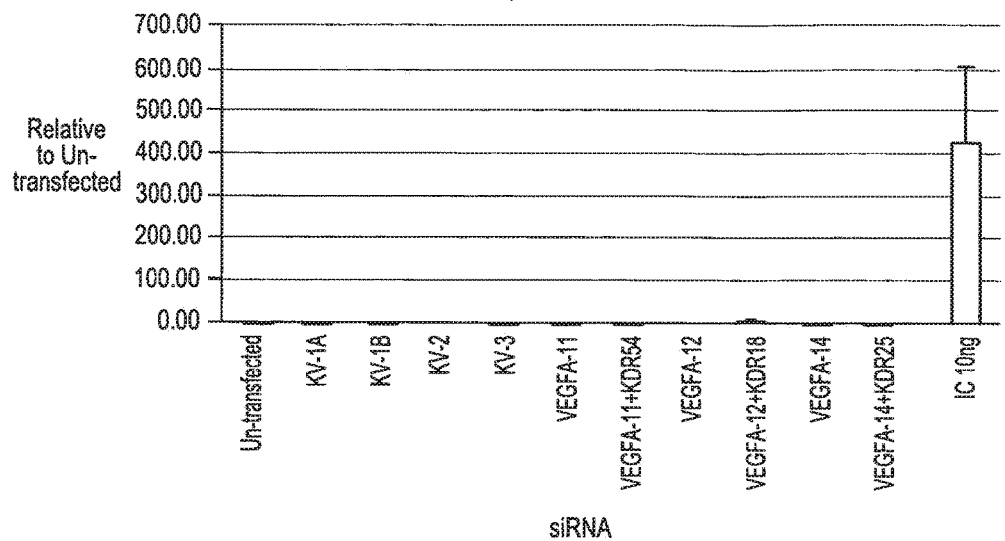
FIG. 5 shows the level of OAS1 induced when iNA constructs disclosed in the specification are transfected into ARPE-19 cells.
Figure 6:
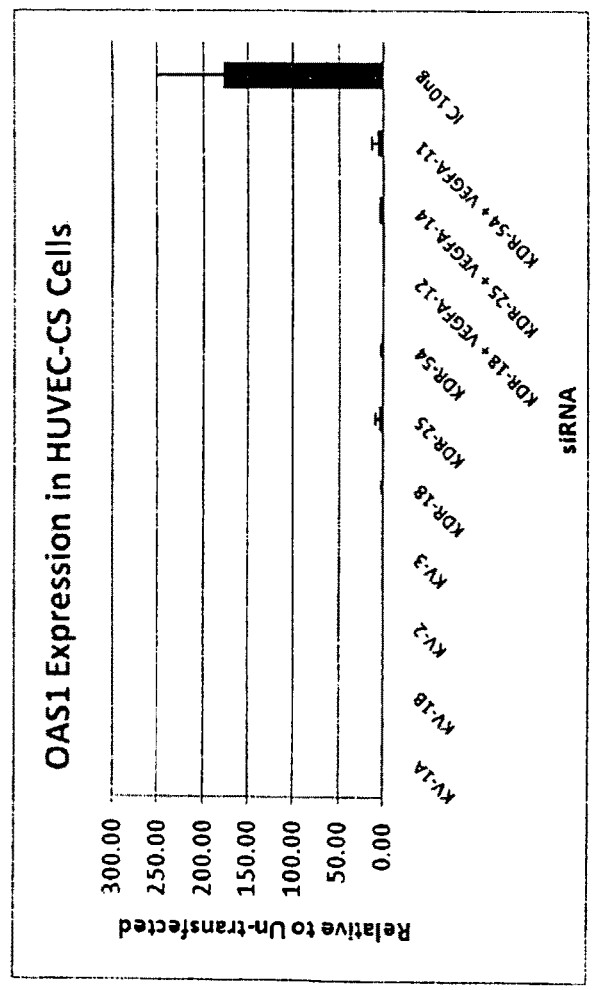
FIG. 6 shows the level of OAS1 induced when iNA constructs disclosed in the specification are transfected into HUVEC-CS cells.
Figure 7:
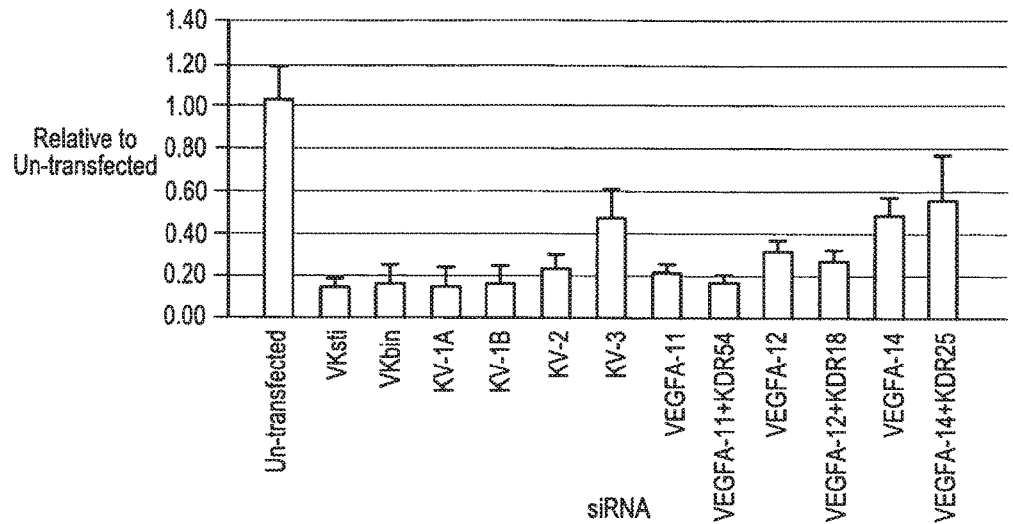
FIG. 7 shows that a long iNA having a segment of the antisense that targets the VEGF A ligand mRNA and a section of the antisense strand that targets the KDR VEGF receptor can mRNA can silence the expression of VEGF A and that iNA constructs that have sense strand segmentation and anti-sense strand segmentation both inhibit the expression of VEGF A in ARPE-19 cells.
Figure 8:
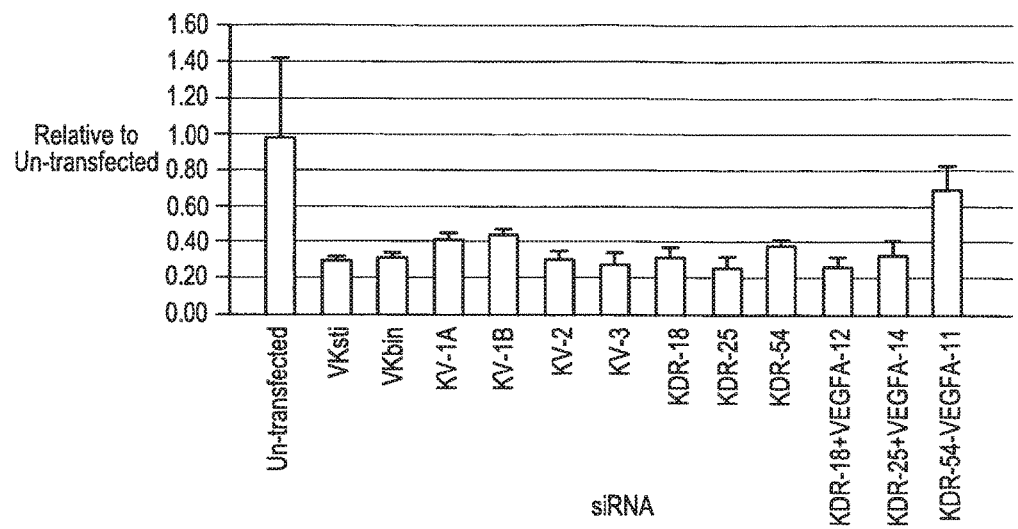
FIG. 8 shows that a long iNA having a segment of the antisense that targets the VEGF A ligand mRNA and a section of the antisense strand that targets the KDR VEGF receptor can mRNA can silence the expression of the KDR VEGF receptor and that iNA constructs that have sense strand segmentation and anti-sense strand segmentation both inhibit the expression of VEGF A in HUVEC-CS cells.
Figure 9:
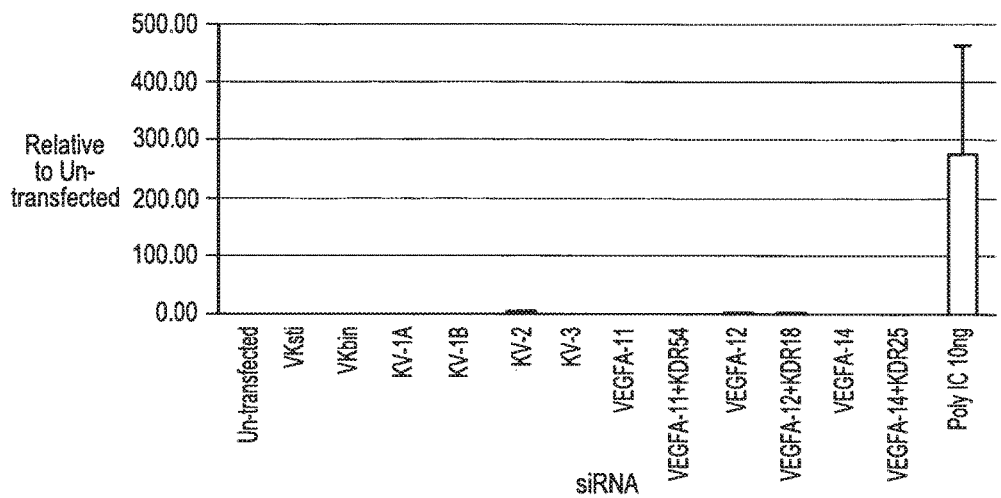
FIG. 9 indicates that the long iNAs having gaps in the sense strand or gaps in the antisense strand do not induce the expression of interferonβ1 when transfected into ARPE-19 cells.
Figure 10:
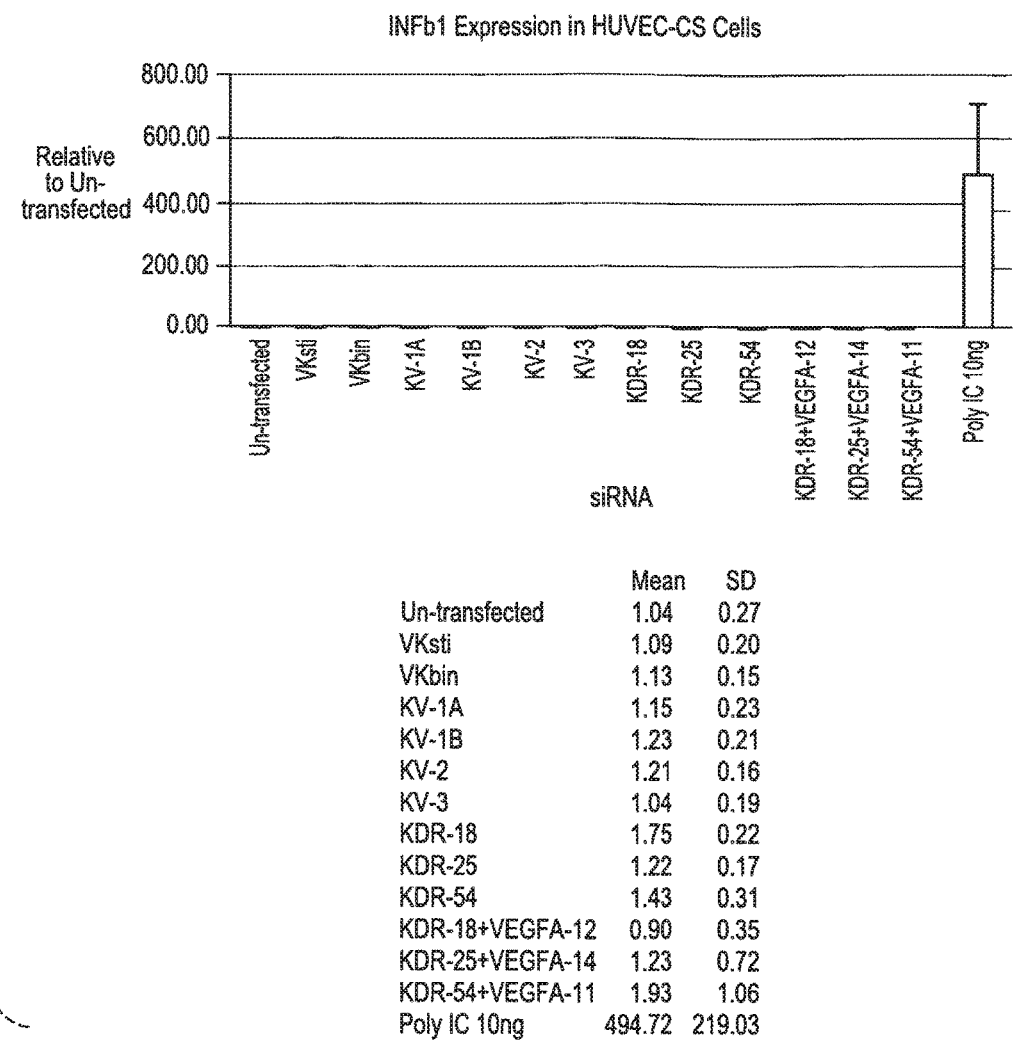
FIG. 10 indicates that the long iNAs having gaps in the sense strand or gaps in the antisense strand do not induce the expression of interferonβ1 when transfected into HUVEC-CS cells.
Figure 11:
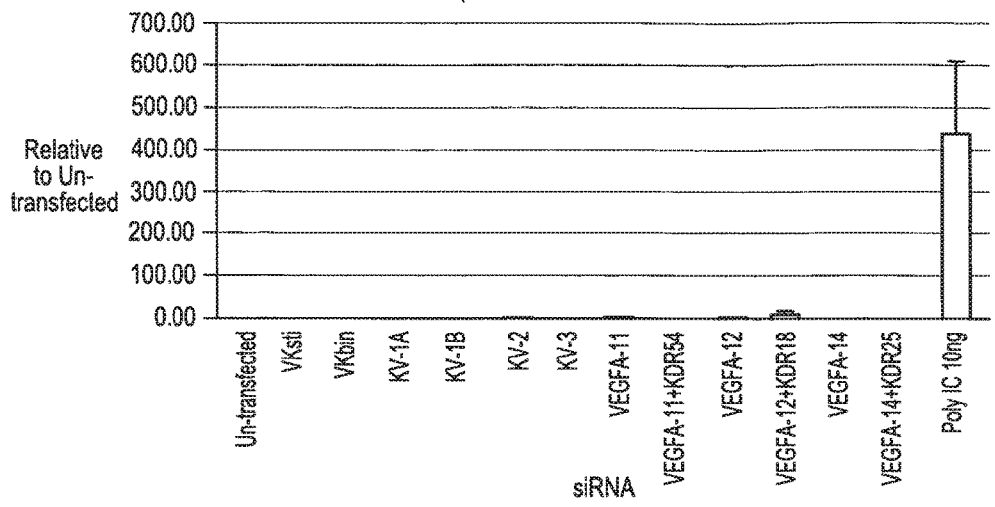
FIG. 11 indicates that the long iNAs having gaps in the sense strand or gaps in the antisense strand do not induce the expression of OAS1 expression when transfected into ARPE-19 cells.
Figure 12:
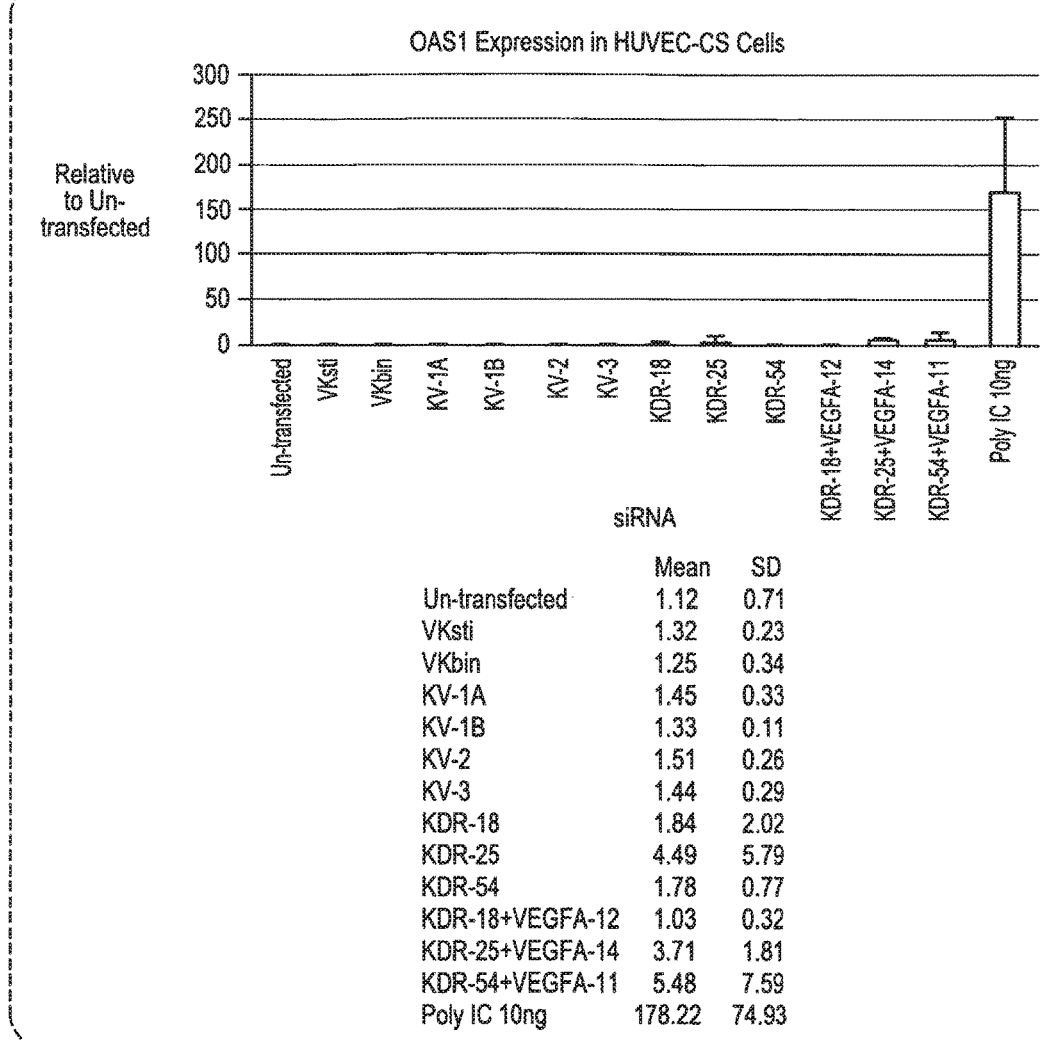
FIG. 12 indicates that the long iNAs having gaps in the sense strand or gaps in the antisense strand do not induce the expression of OAS1 expression when transfected into HUVEC-CS cells.
Figure 13:
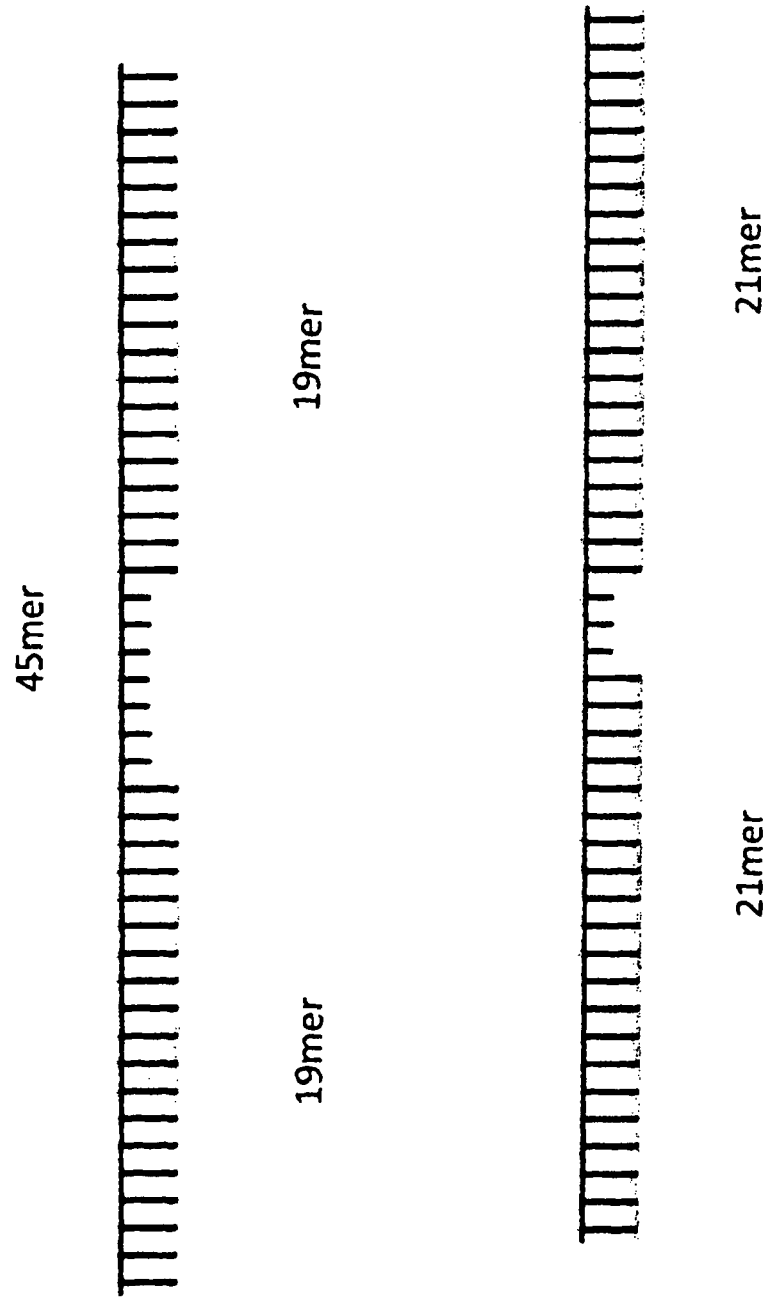
FIG. 13 shows two long iNAs each having a nucleotide gap in the antisense strands, the first antisense strand having a 7-nucleotide gap dividing the antisense strand into two segments, each segment having 19 nucleotides, and a second iNA having an antisense strand that has a 3-nucleotide gap dividing the antisense strand into two segments, each segment having 21 nucleotides.

Definitions of technical terms provided herein should be construed to include without recitation those meanings associated with these terms known to those skilled in the art, and are not intended to limit the scope of the invention.

The use herein of the terms "a," "an," "the," and similar terms in describing the invention, and in the claims, are to be construed to include both the singular and the plural. The terms "comprising," "having," "including," and "containing" are to be construed as open-ended terms which mean, for example, "including, but not limited to."

Recitation of a range of values herein refers individually to each and any separate value falling within the range as if it were individually recited herein, whether or not some of the values within the range are expressly recited. Specific values employed herein will be understood as exemplary and not to limit the scope of the invention.

As used herein, the term interfering nucleic acid (iNA) refers to a nucleic acid duplexes having a sense and antisense strand, which when entered into a RISC complex induces enzymatic degradation of mRNA. Generally each strand contains predominantly RNA nucleotides but the strands can contain RNA analogs, RNA and RNA analogs, RNA and DNA, RNA analogs and DNA, or one strand that is completely DNA and one strand that is RNA as long as the iNA construct induces enzymatic degradation of a homologous mRNA.

As used herein, the term "iNA duplex" is a generic term used throughout the specification to include interfering nucleic acids (iNAs), hairpin iNAs which can be cleaved in vivo to form iNAs. The iNA duplexes herein also include expression vectors (also referred to as iNA expression vectors) capable of giving rise to transcripts which form iNA duplexes or hairpin iNAs in cells, and/or transcripts which can produce iNAs in vivo. Optionally, the iNA include single strands that form a duplex by a hairpin-loop or double strands of iNA. The iNA is a double-stranded polynucleotide molecule comprising self-complementary sense and antisense regions, wherein the antisense region comprises a nucleotide sequence that is complementary to a nucleotide sequence in a target ribonucleic acid molecule for down regulating expression, or a portion thereof. The sense strand or antisense strand have one or more nicks or nucleotide. The terminal structure of iNA may be either blunt or cohesive (overhanging) as long as the iNA can silence the target mRNA. The cohesive (overhanging) end structure is not limited only to the 3' overhang, as the 5' overhanging structure may be included as long as it is capable of inducing the RNAi effect. In addition, the number of overhanging nucleotides is not limited to the reported 2 or 3, but can be any number as long as the overhang is capable of inducing the RNAi effect. For example, the overhang may be 1 to 8, or 2 to 4 nucleotides.

As used herein the length of the iNA duplex is determined by counting the number of nucleotides in the duplex starting at the first base-pair at the 5' end of the sense strand and ending at the last base-pair at the 3' end of the sense strand.

In genetics, microRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Modified nucleotides in an iNA molecule can be in the antisense strand, the sense strand, or both. For example, modified nucleotides can have a Northern conformation (e.g., Northern pseudorotation cycle, see, for example, Saenger, Principles of Nucleic Acid Structure, Springer-Verlag ed., 1984). Examples of nucleotides having a Northern configuration include locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, and 2'-O-methyl nucleotides. Chemically modified nucleotides can be resistant to nuclease degradation while at the same time maintaining the capacity to mediate RNAi. A conjugate molecule attached to a chemically-modified iNA molecule is a polyethylene glycol, human serum albumin, or a ligand for a cellular receptor that can mediate cellular uptake. Examples of specific conjugate molecules contemplated by the instant invention that can be attached to chemically-modified iNA molecules are described in Vargeese, et al., U.S. Patent Publication No. 20030130186 and U.S. Patent Publication No. 20040110296, which are each hereby incorporated by reference in their entirety.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications. For a review see Usman and Cedergren, TIBS 17:34, 1992; Usman, et al, Nucleic Acids Symp. Ser. 31:163, 1994; Burgin, et al, Biochemistry 35:14090, 1996. Sugar modification of nucleic acid molecules have been extensively described in the art. See Eckstein et al., International Publication PCT No. WO 92/07065; Perrault, et al. Nature 344:565-568, 1990; Pieken, et al. Science 253:314-317, 1991; Usman and Cedergren, Trends in Biochem. Sci. 17:334-339, 1992; Usman et al. International Publication PCT No. WO 93/15187; Sproat, U.S. Pat. No. 5,334,711 and Beigelman, et al., J. Biol. Chem. 270:25702, 1995; Beigelman, et al., International PCT Publication No. WO 97/26270; Beigelman, et al., U.S. Pat. No. 5,716,824; Usman, et al., U.S. Pat. No. 5,627,053; Woolf, et al., International PCT Publication No. WO 98/13526; Thompson, et al., Karpeisky, et al, Tetrahedron Lett. 39:1131, 1998; Earnshaw and Gait, Biopolymers (Nucleic Acid Sciences) 48:39-55, 1998; Verma and Eckstein, Annu. Rev. Biochem. 67:99-134, 1998; and Burlina, et al., Bioorg. Med. Chem. 5:1999-2010, 1997. Such publications describe general methods and strategies to determine the location of incorporation of sugar, base and/or phosphate modifications and the like into nucleic acid molecules without modulating catalysis. In view of such teachings, similar modifications can be used as described herein to modify the iNA nucleic acid molecules of the claimed duplexes so long as the ability of iNA to promote RNAi in cells is not significantly inhibited.

The iNA duplexes may contain modified iNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, Nucleic Acid Analogues: Synthesis and Properties, in Modern Synthetic Methods, VCH, 1995, pp. 331-417, and Mesmaeker, et al., "Novel Backbone Replacements for Oligonucleotides, in Carbohydrate Modifications in Antisense Research," ACS, 1994, pp. 24-39. Examples of chemical modifications that can be made in an iNA include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. The antisense region of a iNA molecule can include a phosphorothioate internucleotide linkage at the 3'-end of said antisense region. The antisense region can comprise about one to about five phosphorothioate internucleotide linkages at the 5'-end of said antisense region. The 3'-terminal nucleotide overhangs of a iNA molecule can include ribonucleotides or deoxyribonucleotides that are chemically-modified at a nucleic acid sugar, base, or backbone. The 3'-terminal nucleotide overhangs can include one or more universal base ribonucleotides. The 3'-terminal nucleotide overhangs can comprise one or more acyclic nucleotides. For example, a chemically-modified iNA can have 1, 2, 3, 4, 5, 6, 7, 8, or more phosphorothioate internucleotide linkages in one strand, or can have 1 to 8 or more phosphorothioate internucleotide linkages in each strand. The phosphorothioate internucleotide linkages can be present in one or both oligonucleotide strands of the iNA duplex, for example in the sense strand, the antisense strand, or both strands. In some embodiments, a iNA molecule includes 1, 2, 3, 4, 5, 6, 7, 8, 9, 10, or more purine phosphorothioate internucleotide linkages in the sense strand, the antisense strand, or in both strands.

The iNA molecules, which can be chemically-modified, can be synthesized by: (a) synthesis of two complementary strands of the iNA molecule; and (b) annealing the two complementary strands together under conditions suitable to obtain a double-stranded iNA molecule. In some embodiments, synthesis of the complementary portions of the iNA molecule is by solid phase oligonucleotide synthesis, or by solid phase tandem oligonucleotide synthesis.

Oligonucleotides (e.g., certain modified oligonucleotides or portions of oligonucleotides lacking ribonucleotides) are synthesized using protocols known in the art, for example as described in Caruthers, et al, Methods in Enzymology 211:3-19, 1992; Thompson, et al., International PCT Publication No. WO 99/54459; Wincott, et al., Nucleic Acids Res. 23:2677-2684, 1995; Wincott, et al., Methods Mol. Bio. 74:59, 1997; Brennan, et al., Biotechnol Bioeng. 61:33-45, 1998; and Brennan, U.S. Pat. No. 6,001,311. Synthesis of RNA, including certain iNA molecules of the invention, follows general procedures as described, for example, in Usman, et al., J. Am. Chem. Soc. 109:7845, 1987; Scaringe, et al., Nucleic Acids Res. 18:5433, 1990; and Wincott, et al, Nucleic Acids Res. 23:2677-2684, 1995; Wincott, et al, Methods Mol. Bio. 74:59, 1997. The double-stranded structure may be formed by self-complementary iNA strand such as occurs for a hairpin RNA or by annealing of two distinct complementary iNA strands.

"Overlapping" refers to when two iNA fragments have sequences which overlap by a plurality of nucleotides on one strand, for example, where the plurality of nucleotides (nt) numbers as few as 2-5 nucleotides or by 5-10 nucleotides or more.

"One or more iNAs" refers to iNAs that differ from each other on the basis of primary sequence.

By "target site" or "target sequence" or "targeted sequence" is meant a sequence within a target nucleic acid (e.g., RNA) that is "targeted" for cleavage mediated by an iNA duplex which contains sequences within its antisense region that are complementary to the target sequence.

A nick in a strand is a break in the phosphodiester bond between two nucleotides in the backbone in one of the strands of the duplex of the iNA molecule.

A hybrid iNA molecule is an iNA that is a double-stranded nucleic acid. Instead of a double-stranded RNA molecule, a hybrid iNA is comprised of an RNA strand and a DNA strand. Preferably, the RNA strand is the antisense strand as that is the strand that binds to the target mRNA. The hybrid iNA created by the hybridization of the DNA and RNA strands have a hybridized complementary portion and preferably at least one 3' overhanging end.

To "modulate gene expression" as used herein is to up-regulate or down-regulate expression of a target gene, which can include upregulation or down-regulation of mRNA levels present in a cell, or of mRNA translation, or of synthesis of protein or protein subunits, encoded by the target gene.

The terms "inhibit," "down-regulate," or "reduce expression," as used herein mean that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., iNA) of the invention.

"Gene silencing" as used herein refers to partial or complete inhibition of gene expression in a cell and may also be referred to as "gene knockdown." The extent of gene silencing may be determined by methods known in the art, some of which are summarized in International Publication No. WO 99/32619.

In some embodiments, iNA molecules comprise separate sense and antisense sequences or regions, wherein the sense and antisense regions are covalently linked by nucleotide or non-nucleotide linker molecules, or are non-covalently linked by ionic interactions, hydrogen bonding, van der Waals interactions, hydrophobic interactions, and/or stacking interactions.

The iNAs can be assembled from two separate oligo-nucleotides into a duplex, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the duplex is at least 30 nucleotides in length). The antisense strand may comprise a nucleotide sequence that is complementary to a nucleotide sequence in a target nucleic acid molecule or a portion thereof, and the sense strand may comprise a nucleotide sequence corresponding to the target nucleic acid sequence or a portion thereof. Alternatively, the iNA can be assembled from a single oligonucleotide, where the self-complementary sense and antisense regions of the iNA are linked by means of a nucleic acid-based or non-nucleic acid-based linker(s).

An iNA may be contain a nucleotide, non-nucleotide, or mixed nucleotide/non-nucleotide linker that joins the sense region of the iNA to the antisense region of the iNA. In some embodiments, a nucleotide linker can be 3, 4, 5, 6, 7, 8, 9, or 10 nucleotides in length. In some embodiments, the nucleotide linker can be a nucleic acid aptamer. As used herein, the terms "aptamer" or "nucleic acid aptamer" encompass a nucleic acid molecule that binds specifically to a target molecule, wherein the nucleic acid molecule contains a sequence that is recognized by the target molecule in its natural setting. Alternately, an aptamer can be a nucleic acid molecule that binds to a target molecule where the target molecule does not naturally bind to a nucleic acid. For example, the aptamer can be used to bind to a ligand-binding domain of a protein, thereby preventing interaction of the naturally occurring ligand with the protein. See, for example, Gold, et al., Annu. Rev. Biochem. 64:763, 1995; Brody and Gold, J. Biotechnol. 74:5, 2000; Sun, Curr. Opin. Mol. Ther. 2:100, 2000; Kusser, J. Biotechnol. 74:27, 2000; Hermann and Patel, Science 287:820, 2000; and Jayasena, Clinical Chemistry 45:1628, 1999.

A non-nucleotide linker can be an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, Nucleic Acids Res. 18:6353, 1990, and Nucleic Acids Res. 15:3113, 1987; Cload and Schepartz, J. Am. Chem. Soc. 113:6324, 1991; Richardson and Schepartz, J. Am. Chem. Soc. 113:5109, 1991; Ma, et al., Nucleic Acids Res. 21:2585, 1993, and Biochemistry 32:1751, 1993; Durand, et al., Nucleic Acids Res. 18:6353, 1990; McCurdy, et al, Nucleosides & Nucleotides 10:287, 1991; Jschke, et al., Tetrahedron Lett. 34:301, 1993; Ono, et al., Biochemistry 30:9914, 1991; Arnold, et al., International Publication No. WO 89/02439; Usman, et al., International Publication No. WO 95/06731; Dudycz, et al., International Publication No. WO 95/11910, and Ferentz and Verdine, J. Am. Chem. Soc. 113:4000, 1991. A "non-nucleotide linker" refers to a group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

The term "biodegradable linker" as used herein, refers to a nucleic acid or non-nucleic acid linker molecule that is designed as a biodegradable linker to connect one molecule to another molecule, for example, a biologically active molecule to a iNA molecule or the sense and antisense strands of a iNA molecule. The biodegradable linker is designed such that its stability can be modulated for a particular purpose, such as delivery to a particular tissue or cell type. The stability of a nucleic acid-based biodegradable linker molecule can be variously modulated, for example, by combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof. "Antisense RNA" is an RNA strand having a sequence complementary to a target gene mRNA, that can induce RNAi by binding to the target gene mRNA. Antisense RNA" is an RNA strand having a sequence complementary to a target gene mRNA, and thought to induce RNA by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a 1-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the iNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue. A ribonucleotide is a nucleotide with a hydroxyl group at the 2' position of a R-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of a iNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (join by hydrogen bonding) with each other. By "complementarity" is meant that a nucleic acid can form hydrogen bond(s) with another nucleic acid sequence either by traditional Watson-Crick or by other non-traditional modes of binding.

The sense strand of a double stranded iNA molecule may have a terminal cap moiety such as an inverted deoxyabasic moiety, at the 3'-end, 5'-end, or both 3' and 5'-ends of the sense strand.

By "cap structure" is meant chemical modifications, which have been incorporated at either terminus of the oligonucleotide (see, for example, Adamic, et al, U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety stillben and pyrene.

Examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Lyer, Tetrahedron 49:1925, 1993) and stillben and pyrene.

An "asymmetric hairpin" as used herein is a linear iNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop.

An "asymmetric duplex" as used herein is an iNA molecule having two separate strands comprising a sense region and an antisense region, wherein the sense region comprises fewer nucleotides than the antisense region to the extent that the sense region has enough complementary nucleotides to base pair with the antisense region and form a duplex.

Formulations and Administration

The RNAi-inducing compound of this invention can be administered in conjunction with other known treatments for a disease condition.

Comparable methods and compositions are provided that target expression of one or more different genes associated with a particular disease condition in a subject, including any of a large number of genes whose expression is known to be aberrantly increased as a causal or contributing factor associated with the selected disease condition.

Supplemental or complementary methods for delivery of nucleic acid molecules for use within then invention are described, for example, in Akhtar et al., Trends Cell Bio. 2:139, 1992; "Delivery Strategies for Antisense Oligonucleotide Therapeutics," ed. Akhtar, 1995, Maurer et al., Mol. Membr. Biol. 16:129-140, 1999; Hofland and Huang, Handb. Exp. Pharmacol. 13 7:165-192, 1999; and Lee et al., ACS Symp. Ser. 752:184-192, 2000. Sullivan, et al., International PCT Publication No. WO 94/02595, further describes general methods for delivery of enzymatic nucleic acid molecules.

Nucleic acid molecules can be administered within formulations that include one or more additional components, such as a pharmaceutically acceptable carrier, diluent, excipient, adjuvant, emulsifier, buffer, stabilizer, or preservative.

As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. Examples of ingredients of the above categories can be found in the U.S. Pharmacopeia National Formulary, 1990, pp. 1857-1859, as well as in Raymond C. Rowe, et al., Handbook of Pharmaceutical Excipients, 5th ed., 2006, and "Remington: The Science and Practice of Pharmacy," 21st ed., 2006, editor David B. Troy.

Examples of preservatives include phenol, methyl paraben, paraben, m-cresol, thiomersal, benzylalkonium chloride, and mixtures thereof.

Examples of surfactants include oleic acid, sorbitan trioleate, polysorbates, lecithin, phosphatidylcholines, various long chain diglycerides and phospholipids, and mixtures thereof.

Examples of phospholipids include phosphatidylcholine, lecithin, phosphatidylglycerol, phosphatidylinositol, phosphatidylserine, and phosphatidylethanolamine, and mixtures thereof.

Examples of dispersants include ethylenediaminetetraacetic acid.

Examples of gases include nitrogen, helium, chlorofluorocarbons (CFCs), hydrofluorocarbons (HFCs), carbon dioxide, air, and mixtures thereof.

In certain embodiments, the iNA and/or the polypeptide can be encapsulated in liposomes, administered by iontophoresis, or incorporated into other vehicles, such as hydrogels, cyclodextrins, biodegradable nanocapsules, bioadhesive microspheres, or proteinaceous vectors (see e.g., O'Hare and Normand, International PCT Publication No. WO 00/53722). Alternatively, a nucleic acid composition can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., Clin. Cancer Res. 5:2330-2337, 1999, and Barry et al., International PCT Publication No. WO 99/31262.

The compositions of this invention can be effectively employed as pharmaceutical agents. Pharmaceutical agents prevent, modulate the occurrence or severity of, or treat (alleviate one or more symptom(s) to a detectable or measurable extent) of a disease state or other adverse condition in a patient.

In some embodiments, this invention provides pharmaceutical compositions and methods featuring the presence or administration of one or more polynucleic acid(s), typically one or more iNAs, combined, complexed, or conjugated with a lipid, which may further be formulated with a pharmaceutically-acceptable carrier, such as a diluent, stabilizer, or buffer.

The iNAs of the present invention may be administered in any form, for example transdermally or by local injection (e.g., local injection at sites of psoriatic plaques to treat psoriasis, or into the joints of patients afflicted with psoriatic arthritis or RA). In more detailed embodiments, the invention provides formulations and methods to administer therapeutically effective amounts of iNAs directed against of a mRNA of TNF-α, which effectively down-regulate the TNF-α RNA and thereby reduce or prevent one or more TNF-α-associated inflammatory condition(s). Comparable methods and compositions are provided that target expression of one or more different genes associated with a selected disease condition in animal subjects, including any of a large number of genes whose expression is known to be aberrantly increased as a causal or contributing factor associated with the selected disease condition.

The compositions of the present invention may also be formulated and used as tablets, capsules or elixirs for oral administration, suppositories for rectal administration, sterile solutions, suspensions for injectable administration, and the other forms known in the art.

A pharmacological composition or formulation refers to a composition or formulation in a form suitable for administration, e.g., systemic administration, into a cell or patient, including for example a human. Suitable forms, in part, depend upon the use or the route of entry, for example oral, transdermal, transepithelial, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity.

The iNA molecules can be complexed with cationic lipids, packaged within liposomes, or otherwise delivered to target cells or tissues. The nucleic acid or nucleic acid complexes can be locally administered to through injection, infusion pump or stent, with or without their incorporation in biopolymers. In another embodiment, polyethylene glycol (PEG) can be covalently attached to iNA compounds of the present invention, to the polypeptide, or both. The attached PEG can be any molecular weight, preferably from about 2,000 to about 50,000 daltons (Da).

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular.

Examples of agents suitable for formulation with the nucleic acid molecules of this invention include: P-glycoprotein inhibitors (such as PLURONIC® P85), which can enhance entry of drugs into the CNS (Jolliet-Riant and Tillement, Fundam. Clin. Pharmacol. 13:16-26, 1999); biodegradable polymers, such as poly (DL-lactide-coglycolide) microspheres for sustained release delivery after intracerebral implantation (Emerich, D. F., et al., Cell Transplant 8:47-58, 1999, Alkermes, Inc., Cambridge, Mass.); and loaded nanoparticles, such as those made of polybutylcyanoacrylate, which can deliver drugs across the blood brain barrier and can alter neuronal uptake mechanisms (Prog. Neuropsychopharmacol Biol. Psychiatry 23:941-949, 1999). Other examples of delivery strategies for the nucleic acid molecules of the instant invention include material described in Boado, et al., J. Pharm. Sci. 87:1308-1315, 1998; Tyler, et al., FEBS Lett. 421:280-284, 1999; Pardridge, et al., PNAS USA. 92:5592-5596, 1995; Boado, Adv. Drug Delivery Rev. 15:73-107, 1995; Aldrian-Herrada et al., Nucleic Acids Res. 26:4910-4916, 1998; and Tyler, et al., PNAS USA. 96:7053-7058, 1999.

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro ed. 1985). For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, treat, or alleviate a symptom to some extent of a disease state. An amount of from 0.01 mg/kg to 50 mg/kg body weight/day of active nucleic acid should be administered.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The iNAs can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Methods for the delivery of nucleic acid molecules are described in Akhtar, et al., Trends Cell Bio. 2:139, 1992; "Delivery Strategies for Antisense Oligonucleotide Therapeutics," ed. Akhtar, 1995; Maurer, et al., Mol. Membr. Biol. 16:129-140, 1999; Hofland and Huang, Handb. Exp. Pharmacol. 137:165-192, 1999; and Lee, et al., ACS Symp. Ser. 752:184-192, 2000. Beigelman, et al., U.S. Pat. No. 6,395,713, and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example, Gonzalez, et al., Bioconjugate Chem. 10:1068-1074, 1999; Wang, et al., International PCT Publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry, et al., Clin. Cancer Res. 5:2330-2337, 1999, and Barry, et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

Determining the Length of an iNA Duplex

As stated above, the length of the iNA duplex is determined by counting the number of nucleotides in the duplex starting at the first base-pair at the 5' end of the sense strand and ending at the last base-pair at the 3' end of the sense strand regardless of any nicks or nucleotide gaps between the first and last base pairs.

Designing of iNA Duplexes Targeting Multiple mRNAs

Because the claimed iNA duplexes are at least 30 nucleotides in length and do not induce an interferon response when transfected into mammalian cells, iNA duplexes can be effectively designed that target two or more mRNA transcripts. One segment of the antisense can be complementary to one mRNA transcript and another segment of the antisense strand can be complementary to another mRNA. Furthermore, the sense strand can be designed so that one or more segments are long enough to enter RISC and bind to a target mRNA.

The examples given herein, and the exemplary language used herein are solely for the purpose of illustration, and are not intended to limit the scope of the invention.

While this invention has been described in relation to certain embodiments, and many details have been set forth for purposes of illustration, it will be apparent to those skilled in the art that this invention includes additional embodiments, and that some of the details described herein may be varied considerably without departing from this invention. This invention includes such additional embodiments, modifications and equivalents. In particular, this invention includes any combination of the features, terms, or elements of the various illustrative components and examples.

Example 1

An iNA Having a Segmented Sense Strand a First Segment of the Antisense Strand Targeted to KDR mRNA and a Second Segment of the Antisense Strand Targeted to the VEGF A mRNA The following constructs illustrate the design of single iNA that target multiple mRNAs that encode polypeptides associated with angiogenesis.

Design of KV-1A iNA Targeting KDR-54 and VEGF A-11

SEQ ID NO: 1 shows an antisense sequence of an iNA that has a first 3'-segment (refer to anti-sense strand) that can to and target an mRNA that encodes VEGF, and a second 5'-segment (refer to anti-sense strand) that can anneal to and target an mRNA that encodes the receptor KDR.

(SEQ ID NO: 1)
5' UUCUACAUCACUGAGGGACdTdTcucAUUUACACGUCUGCGG
AUCUU 3'

SEQ ID NO:2 is a sense nucleotide sequence that anneals to a the segment of the antisense sequence SEQ ID NO:1 that targets the KDR mRNA.

KV-1KS:
(SEQ ID NO: 2)
GUCCCUCAGUGAUGUAGAAdTdT

SEQ ID NO:3 is a sense nucleotide sequence that anneals to a the segment of the antisense sequence SEQ ID NO: 1 that targets the VEGF mRNA.

KV-1VS:
(SEQ ID NO: 3)
AAGAUCCGCAGACGUGUAAAU

Using SEQ ID NOs: 1-3 the following iNA duplex was made (iNA Duplex VEGF A-11 and KDR-54 iNA)

(SEQ ID NO: 3)
5'AAGAUCCGCAGACGUGUAAAU (SEQ ID NO: 2)
GUCCCUCAGUGAUGUAGAATT 3'

-continued
(SEQ ID NO: 1)
3'UUCUAGGCGUCUGCACAUUUACUCTTCAGGGAGUCACUACAUCUU 5'

Example 2

An iNA Having a First 3'-Segment of the Antisense Strand Targeted to KDR mRNA and a Second 5'-Segment of the Antisense Strand Targeted to the VEGF A mRNA KV-1B iNA (KDR-54+VEGF A-11):

SEQ ID NO: 4 shows an antisense sequence of an iNA that has a 3'-first segment that can to and target an mRNA that encodes VEGF, and a second 5'-segment that can anneal to and target an mRNA that encodes the receptor KDR.

(SEQ ID NO: 4)
UUCUACAUCACUGAGGGACUUcucAUUUACACGUCUGCGGAUCUU

SEQ ID NO:5 is a sense nucleotide sequence that anneals to a the segment of the antisense sequence SEQ ID NO:4 that targets the KDR mRNA.

KV-1KS:
(SEQ ID NO: 5)
GUCCCUCAGUGAUGUAGAAdTdT

SEQ ID NO:6 is a sense nucleotide sequence that anneals to a the segment of the antisense sequence SEQ ID NO:4 that targets the VEGF mRNA.

KV-1VS:
(SEQ ID NO: 6)
AAGAUCCGCAGACGUGUAAAU

Using SEQ ID NOs: 4-6 the following iNA duplex was made KV-1B iNA (KDR-54+VEGF A-11)

(SEQ ID NO: 6)
5' AAGAUCCGCAGACGUGUAAAU (SEQ ID NO: 5)
GUCCCUCAGUGAUGUAGAATT 3'

(SEQ ID NO: 4)
3' UUCUAGGCGUCUGCACAUUUACUCUUCAGGGAGUCACUACAUC
UU 5'

Example 3

An iNA Having a First 5'-Segment of the Antisense Strand Targeted to KDR mRNA and a Second 3'-Segment of the Antisense Strand Targeted to the VEGF A mRNA SEQ ID NO: 7 shows an antisense sequence of an iNA that has a first 3'-segment that can to and target an mRNA that encodes VEGF, and a second 5'-segment that can anneal to and target an mRNA that encodes the receptor KDR.

KV-2 (KDR-18 + VEGF A-12):

(SEQ ID NO: 7)
UGUUGCUCCUUCUUUCAACdAdTuuuUUUGCAGGAACAU
UUACACGU

SEQ ID NO:8 is a sense nucleotide sequence that anneals to a the segment of the antisense sequence SEQ ID NO:7 that targets the KDR mRNA.

KV-2KS:

(SEQ ID NO: 8)
GUUGAAAGAAGGAGCAACAdTdT

SEQ ID NO:9 is a sense nucleotide sequence that anneals to a the segment of the antisense sequence SEQ ID NO:7 that targets the VEGF mRNA.

KV-2VS:

(SEQ ID NO: 9)
ACGUGUAAAUGUUCCUGCAAA

Using SEQ ID NOs: 7-9 the following iNA duplex was made KV-1B iNA (KDR-18+VEGF A-12)

(SEQ ID NO: 9)
5' ACGUGUAAAUGUUCCUGCAAA (SEQ ID NO: 8)
GUUGAAAGAAGGAGCAACATT 3'

(SEQ ID NO: 7)
3' UGCACAUUUACAAGGACGUUUUUUTACAACUUUCUUCCUCGUU
GU 5'

Example 4

An iNA Having a First 5'-Segment of the Antisense Strand Targeted to KDR mRNA and a Second 3'-Segment of the Antisense Strand Targeted to the VEGF A mRNA

KV-3 (KDR-25+VEGF A-14):

SEQ ID NO: 10 shows an antisense sequence of an iNA that has a first 3'-segment that can to and target an mRNA that encodes VEGF, and a second 5'-segment that can anneal to and target an mRNA that encodes the receptor KDR.

KV-3AS:

(SEQ ID NO: 10)
UUCAAAUGUUUUUACACUCdAdCagcACAUCUGCAAGUACGUUCGUU

SEQ ID NO: 11 is a sense nucleotide sequence that anneals to a the segment of the antisense sequence SEQ ID NO:10 that targets the KDR mRNA.

KV-3KS:

(SEQ ID NO: 11)
GAGUGUAAAAACAUUUGAAdTdT

SEQ ID NO:12 is a sense nucleotide sequence that anneals to a the segment of the antisense sequence SEQ ID NO:10 that targets the VEGF mRNA.

KV-3VS:

(SEQ ID NO: 12)
AACGAACGUACUUGCAGAUGU

Using SEQ ID NOs: 7-9 the following iNA duplex was made KV-3 iNA (KDR-25+VEGF A-14)

(SEQ ID NO: 12)
5' AACGAACGUACUUGCAGAUGU (SEQ ID NO: 11)
GAGUGUAAAAACAUUUGAATT 3'

(SEQ ID NO: 10)
3' UUGCUUGCAUGAACGUCUACACGACACUCACAUUUUUGUAAAC
UU 5'

Example 5

NT-VEGF A-11
Sense:
(SEQ ID NO: 13)
GAUCCGCAGACGUGUAAAUdTdT

Anti-sense:
(SEQ ID NO: 14)
AUUUACACGUCUGCGGAUCdTdT (SEQ ID NO: 13)
5' GAUCCGCAGACGUGUAAAUTT 3'

(SEQ ID NO: 14)
3' TTCUAGGCGUCUGCACAUUUA 5'

Example 6

NT-VEGF A-12
Sense:
(SEQ ID NO: 15)
GUGUAAAUGUUCCUGCAAAdTdT

Anti-sense:
(SEQ ID NO: 16)
UUUGCAGGAACAUUUACACdGdT (SEQ ID NO: 15)
5' GUGUAAAUGUUCCUGCAAAdTdT 3'

(SEQ ID NO: 16)
3' TGCACAUUUACAAGGACGUUU 5'

Example 7

NT-VEGF A-14
Sense:
(SEQ ID NO: 17)
CGAACGUACUUGCAGAUGUdTdT

Anti-sense:
(SEQ ID NO: 18)
ACAUCUGCAAGUACGUUCGdTdT (SEQ ID NO: 17)
5' CGAACGUACUUGCAGAUGUdTdT 3'

```
                                             (SEQ ID NO: 18)
3' TTGCUUGCAUGAACGUCUACA 5'
```

Example 8

```
KDR-18
Sense:
                                             (SEQ ID NO: 19)
GUUGAAAGAAGGAGCAACAdTdT Anti-sense:
                                             (SEQ ID NO: 20)
UGUUGCUCCUUCUUUCAACdAdT (SEQ ID NO: 19)
5' GUUGAAAGAAGGAGCAACATT 3'

(SEQ ID NO: 20)
3' TACAACUUUCUUCCUCGUUGU 5'
```

Example 9

```
KDR-25
Sense:
                                             (SEQ ID NO: 21)
GAGUGUAAAAACAUUUGAAdTdT Anti-sense:
                                             (SEQ ID NO: 22)
UUCAAAUGUUUUUACACUCdAdC (SEQ ID NO: 21)
5' GAGUGUAAAAACAUUUGAATT (SEQ ID NO: 22)
3' CACUCACAUUUUUGUAAACUU
```

Example 10

```
KDR-54
Sense:
                                             (SEQ ID NO: 23)
GUCCCUCAGUGAUGUAGAAdTdT Anti-sense:
                                             (SEQ ID NO: 24)
UUCUACAUCACUGAGGGACdTdT (SEQ ID NO: 23)
5' GUCCCUCAGUGAUGUAGAAdTdT (SEQ ID NO: 24)
3' TTCAGGGAGUCACUACAUCUU
``` siRNA Concentration:
KV1A, B, 2, 3: 10 nM
All the other siRNA: 10 nM
Experimental Methods
mRNA isolation: Cells were washed once with 100 μL PBS and then 70 μL of lysis buffer (SPY4, Sigma) was added. The lysate (60 μL) was transferred to a 96-well mRNA capture plate and incubated for 1-2 hours at room temperature. After decanting the lysate, the plate was washed three times with 80 μL wash buffer each. Then 60 μL of elution buffer was added to each well and incubated at 65° C. for 5 minutes. The elution solution (containing mRNA) was transferred to new 96-well clear plate.

Cells are harvested at 48 hrs after transfection. Check cell confluency before harvest. Then, remove media and add 90 μl TCL cell lysis buffer to each well. Keep at room temperature for 20 min. Transfer 80 μl lysate into each well of TURBOCAPTURE® plate (Qiagen, Cat#: 72251). Keep in room temperature for 60 min. Then wash three times with TCW buffer with 100 μl for each wash. Add 80 μl TCE buffer and keep in 65° C. for 5 min. Transfer 80 μl elution solution into new 96-well plate.

qRT-PCR:

1 μL of isolated mRNA was used to run RT-PCR with SYBR Green one-step qRT-PCR kit (SENSIMIX® one-step SYBR Green kit, Bioline) by mixing with 13 μL master mix containing 7 μL of 2× master mix (containing reverse transcriptase), 1 μL forward and reverse primer (6 μM), 0.3 μL 50×SYBR Green and 4.7 μL water. The reverse transcription reaction took place at 42° C., 30 min; after another 95° C., 10 min; the thermocyle of reaction of 95° C., 15 sec; 60° C., 30 sec; 72° C., 20 sec; 50 cycles was used. Taking 4 μl diluted mRNA to run qRT-PCR with Bioline one-step qRT-PCR kit. Reaction size: 14 μl.

7 μl 2× master mix (ABI, Cat #: 4309169)

0.3 μl 50×SYBR Green 0.35 μl F+R primer (6 μM)

1.7 μl water

42° C., 30 min; 95° C., 10 min; 95° C., 15 sec; 60° C., 20 sec; 72° C., 20 sec; 50 cycles, then melt curve.

KDR-VEGF A iNA (KV-1A, KV-1B, KV-2, KV-3) is as Good as Standard siRNA in Knockdown KDR and VEGF A Gene Expression VEGF A-11 works better than VEGF A-12, 14

KDR-18 and KDR-25 works similarly, both are better than KDR-54

None of iNA induce INFb1 or OAS1 significantly in ARPE-19 or HUVEC-CS cells

Measuring Interferon-Response

At 48 hours post-transfection the level of mRNA encoding interferon was measured using RT-PCR. The cells were washed once with 100 μL PBS and then 70 μL of lysis buffer (SPY4, Sigma) was added. The lysate (60 μL) was transferred to a 96-well mRNA capture plate and incubated for 1-2 hours at room temperature. After decanting the lysate, the plate was washed three times with 80 μL wash buffer each. Then 60 μL of elution buffer was added to each well and incubated at 65° C. for 5 minutes. The elution solution (containing mRNA) was transferred to new 96-well clear plate.

Real-time RT-PCR: The level of mRNA encoding interferon was determined by RT-PCT wherein 1 μL of isolated mRNA was used to run RT-PCR with SYBR Green one-step qRT-PCR kit (SENSIMIX® one-step SYBR Green kit) by mixing with 13 μL master mix containing 7 μL of 2× master mix (containing reverse transcriptase), 1 μL forward and reverse primer (6 μM), 0.3 μL 50×SYBR Green and 4.7 μL water. The reverse transcription reaction took place at 5042° C., 30 min; after another 95° C., 15 min 10 min; the thermocyle of reaction of 95° C., 15 sec; 5560° C., 30 sec; 72° C., 30 sec 20 sec; 40 50 cycles was used. For interferon response, interferon β1gene and OAS1 gene were used. The primers used to detect the level of interferon β1genes by QRTqRT-PCR were:

```
Forward primer:
                                      (SEQ ID NO: 25)
    TTTGACATCCCTGAGGAGATT
Reverse primer:
                                      (SEQ ID NO: 26)
    GATAGACATTAGCCAGGAGGTT
```

The primers used to detect the level of OAS1 genes by qRT-PCR were:

```
Forward primer:
                                      (SEQ ID NO: 27)
    GTGAGCTCCTGGATTCTGCT
Reverse primer:
                                      (SEQ ID NO: 28)
    TGTTCCAATGTAACCATATTTCTGA
```

Experimental Purpose

Compare knockdown and interference response of the selected siRNA and the iNA constructs.

Experimental Methods

Cells: ARPE-19 cells (passage#: 5) and HUVEC-CS (passage#: 3) plated (96-well plate) overnight. The cell confluency for both the cell lines is 40% at the moment for transfection next morning.

Transfection:

siRNA diluted in 10 µl OPTI-MEM®. RNAiMAX™ (0.2 µl/well; Invitrogen) diluted into 10 µl OPTI-MEM® and keep for 5 min at room temperature. Mix above two by vortexing 10 sec and keep in room temperature for 10 min. Add 20 µl transfection complex to each well which has 80 µl OPTI-MEM®. Four hours later, add 100 µl complete media to each well, then replaced with 100 µl complete media in following morning.

Example 11

Comparison of iNA (Sense or Anti-Sense Segmentation) and siRNA in Knockdown of Gene Expression and Interferon Response Introduction Experimental Purpose Compare knockdown and interference response of the selected siRNA and the iNA constructs (sense segmentation and anti-sense segmentation)

Experimental Methods

Cells: ARPE-19 cells (passage#: 3) and HUVEC-CS (passage#: 2) plated (96-well plate) overnight. The cell confluency for both the cell lines is 40% at the moment for transfection next morning.

Transfection:

siRNA diluted in 10 µl OPTI-MEM®. iNTFect (0.5 µl/well) diluted into 10 µl OPTI-MEM® and keep for 5 min at room temperature. Mix above two by vortexing 10 sec and keep in room temperature for 10 min. Add 20 µl transfection complex to each well which has 80 µl OPTI-MEM®. Four hours later, add 100 µl complete media to each well, then replaced with 100 µl complete media in following morning.

Experimental Methods

```
siRNA:
Vksti (VEGF A-11 + KDR-25)
Vksti-S:
                                      (SEQ ID NO: 29)
    GAUCCGCAGACGUGUAAAUdTdTuguGAGUGUAAAAACAUUUGAAdTdT
VEGF A-11AS:
                                      (SEQ ID NO: 14)
    AUUUACACGUCUGCGGAUCdTdT
KDR-25 AS:
                                      (SEQ ID NO: 22)
    UUCAAAUGUUUUACACUCdAdC
Vkbln (VEGF A-11 + KDR-25)
Vksti-S:
                                      (SEQ ID NO: 30)
    GAUCCGCAGACGUGUAAAUdTdTuguGAGUGUAAAAACAUUUGAA
VEGF A-11AS:
                                      (SEQ ID NO: 14)
    AUUUACACGUCUGCGGAUCdTdT
KDR-25 AS:
                                      (SEQ ID NO: 22)
    UUCAAAUGUUUUACACUCdAdC
KV-1A (KDR-54 + VEGF A-11):
KV-1AS:
                                      (SEQ ID NO: 31)
    UUCUACAUCACUGAGGGACdTdTcucAUUUACACGUCUGCGGAUCUU
KV-1KS:
                                      (SEQ ID NO: 2)
    GUCCCUCAGUGAUGUAGAAdTdT
KV-1VS:
                                      (SEQ ID NO: 3)
    AAGAUCCGCAGACGUGUAAAU
KV-1B (KDR-54 + VEGF A-11):
K-1AS:
                                      (SEQ ID NO: 32)
    UUCUACAUCACUGAGGGACUUcucAUUUACACGUCUGCGGAUCUU
KV-1KS:
                                      (SEQ ID NO: 2)
    GUCCCUCAGUGAUGUAGAAdTdT
KV-1VS:
                                      (SEQ ID NO: 3)
    AAGAUCCGCAGACGUGUAAAU
KV-2 (KDR-18 + VEGF A-12):
KV-2AS:
                                      (SEQ ID NO: 33)
    UGUUGCUCCUUCUUUCAACdAdTuuuUUUGCAGGAACAUUUACACGU
KV-2KS:
                                      (SEC ID NO: 8)
    GUUGAAAGAAGGAGCAACAdTdT
KV-2VS:
                                      (SEQ ID NO: 9)
    ACGUGUAAAUGUUCCUGCAAA
KV-3 (KDR-25 + VEGF A-14):
KV-3AS:
                                      (SEQ ID NO: 34)
    UUCAAAUGUUUUACACUCdAdCagcACAUCUGCAAGUACGUUCGUU
KV-3KS:
                                      (SEQ ID NO: 11)
    GAGUGUAAAAACAUUUGAAdTdT
KV-3VS:
                                      (SEQ ID NO: 12)
    AACGAACGUACUUGCAGAUGU
```

```
NT-VEGF A-11
Sense:
                                          (SEQ ID NO: 13)
GAUCCGCAGACGUGUAAAUdTdT Anti-sense:
                                          (SEQ ID NO: 14)
AUUUACACGUCUGCGGAUCdTdT NT-VEGF A-12
Sense:
                                          (SEQ ID NO: 15)
GUGUAAAUGUUCCUGCAAAdTdT Anti-sense:
                                          (SEQ ID NO: 16)
UUUGCAGGAACAUUUACACdGdT NT-VEGF A-14
Sense:
                                          (SEQ ID NO: 17)
CGAACGUACUUGCAGAUGUdTdT Anti-sense:
                                          (SEQ ID NO: 18)
ACAUCUGCAAGUACGUUCGdTdT KDR-18
Sense:
                                          (SEQ ID NO: 19)
GUUGAAAGAAGGAGCAACAdTdT Anti-sense:
                                          (SEQ ID NO: 20)
UGUUGCUCCUUCUUUCAACdAdT KDR-25
Sense:
                                          (SEQ ID NO: 21)
GAGUGUAAAACAUUUGAAdTdT Anti-sense:
                                          (SEQ ID NO: 22)
UUCAAAUGUUUUUACACUCdAdC KDR-54
Sense:
                                          (SEQ ID NO: 23)
GUCCCUCAGUGAUGUAGAAdTdT Anti-sense:
                                          (SEQ ID NO: 24)
UUCUACAUCACUGAGGGACdTdT
``` iRNA Concentration:

KV1A, B, 2, 3: 10 nM

All the siRNA: 10 nM iNA of Segmented Anti-Sense Strand

VEGF A-11+KDR-25 with 3 nt Gap and Stick End

```
                                          (SEQ ID NO: 35)
5'-GAUCCGCAGACGUGUAAAUdTdTuguGAGUGUAAAAACAUUUGAAd
TdT-3'

(SEQ ID NO: 14)
3'-dTdTCUAGGCGUCUGCACAUUUA-5'

(SEQ ID NO: 22)
3'-dCdACUCACAUUUUUGUAAACUU-5'
```

VEGF A-11+KDR-25 with 4 nt Gap and One Blunt End

```
                                          (SEQ ID NO: 36)
5'-GAUCCGCAGACGUGUAAAUdTdTcuguGAGUGUAAAAACAUUUGAA-
3'

(SEQ ID NO: 14)
3'-dTdTCUAGGCGUCUGCACAUUUA-5'

(SEQ ID NO: 22)
3'-dCdACUCACAUUUUUGUAAACUU-5'
```

VEGF A+KDR-25+PDGFRB-16 with 3 nt Gap and Blunt End

```
                                          (SEQ ID NO: 37)
5'GAUCCGCAGACGUGUAAAUdTdTuguGAGUGUAAAAACAUUUGAAdTd
TacgAGAUCUAUGAGAUCAUGCA3'

(SEQ ID NO: 14)
3'dTdTCUAGGCGUCUGCACAUUUA (SEQ ID NO: 22)
dCdACUCACAUUUUUGUAAACUU (SEQ ID NO: 38)
dGdCUCUAGAUACUCUAGUACGU 5'
```

U, A, G, C are RNA bases; dT, dA, dC and dG are DNA bases

Standard iNA design usually features a 10-27 base pair contiguous double strand region that is believed to be important for RISC incorporation. Studies have shown that iNAs duplexes longer than 30 base pair double strand RNA can cause interferon response. Therefore it was necessary to use iNAs duplexes shorter than 30 base pairs to prevent interferon response. Here we described a novel design in which a strand longer than 30 base paired RNA complement with two more strand(s) separated by either nick or gap(s) improves silencing property without causing interferon response in both the sense and antisense strands. A 30 mer contiguous double strand RNA causes interferon response as indicated by increased expression level of interferon β. With same sequence and new design in which two or more sense strands or two more antisense strands separated with either gap or nick and complement with a long contiguous sense or antisense strands, the interferon response was diminished. Moreover, when using the novel iNA duplexes of the present invention, one can target more than one site in the same mRNA or more than one mRNA. The novel iNAs of the present invention have the therapeutic potential to treat viral or bacterial diseases that have a number of mutated forms or diseases wherein the down-regulation of multiple genes would be desirable.

Example 13

Knockdown of LacZ Gene Expression and Analysis of Interferon Response of iNAs Having a Stilbene or Pyrrolindol Linked to One or More Nucleotides Overview A number of iNAs of were designed and synthesized to suppress the expression of the LacZ gene in 9 L/LacZ cells (A rat gliosarcoma cell line, ATCC #CRL-2200. These iNAs were transfected into cells expressing the LacZ gene to see if they could silence the expression of the LacZ gene. The full-length DNA sequence of the LacZ gene is shown below.

Figure 15:
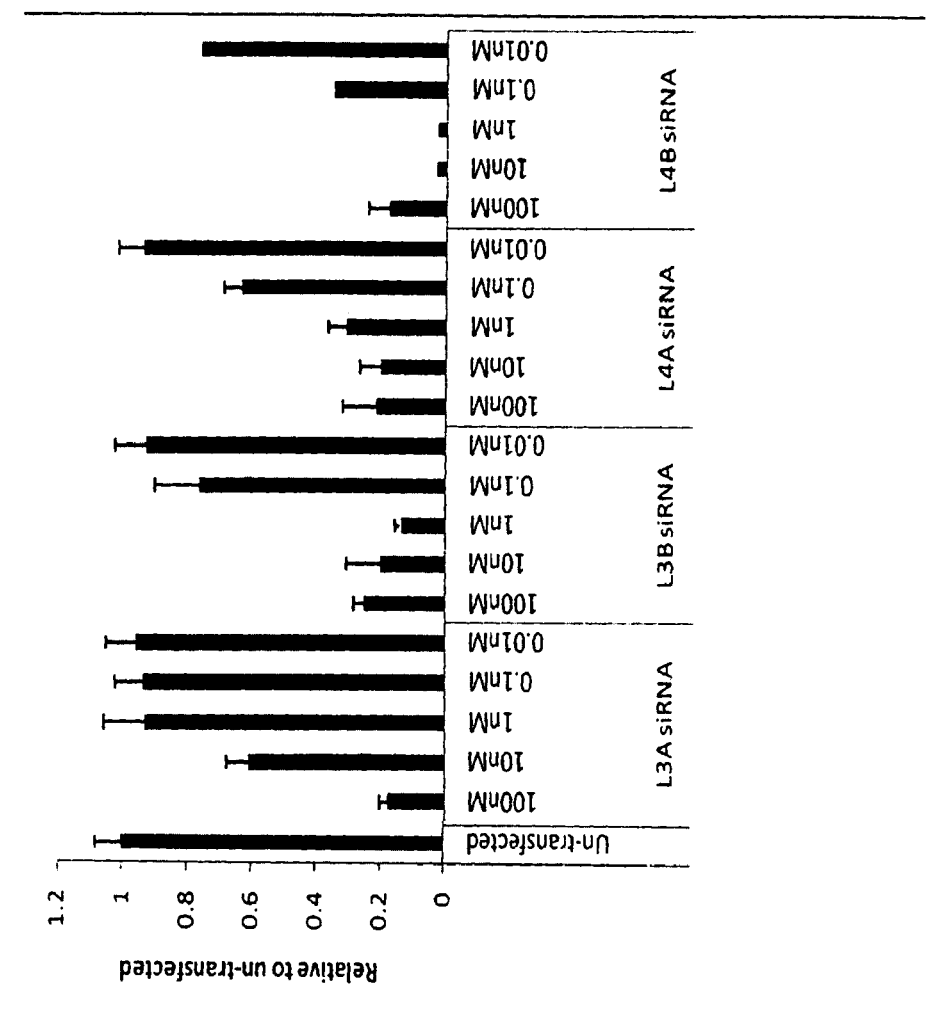
FIG. 15 shows a functional analysis of the knockdown of LacZ gene expression and of iNAs having a stilbene or pyrrolindol linked to one or more nucleotides.

Each of the iNAs were placed in separate wells of a 96-well plate containing 9 L/LacZ cells which expressed the LacZ gene under conditions wherein the iNAs were transfected into the 9 L/LacZ cells as described below in the procedure section. FIG. 15 shows the level of suppression of the LacZ gene caused by each of the iNAs. FIG. 15 shows that all of the iNA duplexes were able to reduce the expression of the LacZ gene, especially at a concentration of 0.1 nM or greater and that construct L3B was more effective than construct L3A, and construct L4B was more effective than construct L4A. The procedures used to transfect the iNA duplexes into the 9 L cells are described below.

Cell Culture:

9 L/LacZ cells were grown in DMEM supplemented with 10% FBS at 37° C., supplied with 5% $CO_2$.

Transfection:

9 L/LacZ cells were plated in a 96-well plate and grown overnight. The cells were about 20% (9 L/LacZ) confluency at the time of transfection.

The different amounts of iNA transfected into the 9 L/LacZ cells were 100 nM, 10 nM, 1 nM, 0.1 nM, and 0.01 nM, which had been diluted in 10 µL OPTI-MEM®. In a separate microcentrifuge tube, transfection reagents (RNAiMAX™, Invitrogen) were diluted in 10 µL OPTI-MEM® also and kept in room temperature for 5 minutes. The contents of each tube were combined and vortexed for approximately 10 seconds and then incubated for 10-15 minutes at room temperature. Then the transfection complex was added to each well which has 80 µL OPTI-MEM®. The cells were allowed to be incubated with the transfection mixture for four hours. Fresh media (100 µL) was added to each well. Following morning, fresh growth media (100 µL) was replaced for each well.

β-Galactosidase Assay

Three days after transfection, the 9 L/LacZ cells were harvested. The cells were washed once with 100 µL phosphate buffered saline (PBS) and lysed with 70 µL M-PER® Reagent (Pierce). 20 µL of lysate was transferred from each well to new 96-well plate for protein assay with micro BCA kit (Pierce). 30 µL lysate was taken from each well to put in another new plate and add 30 µL ALL-IN-ONE™ β-Galactosidase Assay Reagent (Pierce) to each well. Cover plate and incubate for 30-40 minutes at 37° C. and light absorbance the absorbance was measured at 405 nm.

Micro BCA Assay:

To measure total protein within the 9 L/LacZ cells, 20 µL of cell lysate was transferred to each well of a 96-well plate, 130 µL of water was added to each well, and 150 µL Micro BCA (Pierce) working solution (25:24:1 of Reagent A:B:C) was added to each well and incubated at 37° C. for 2 hours and then the light absorbance was measured at 562 nm.

Figure 14:
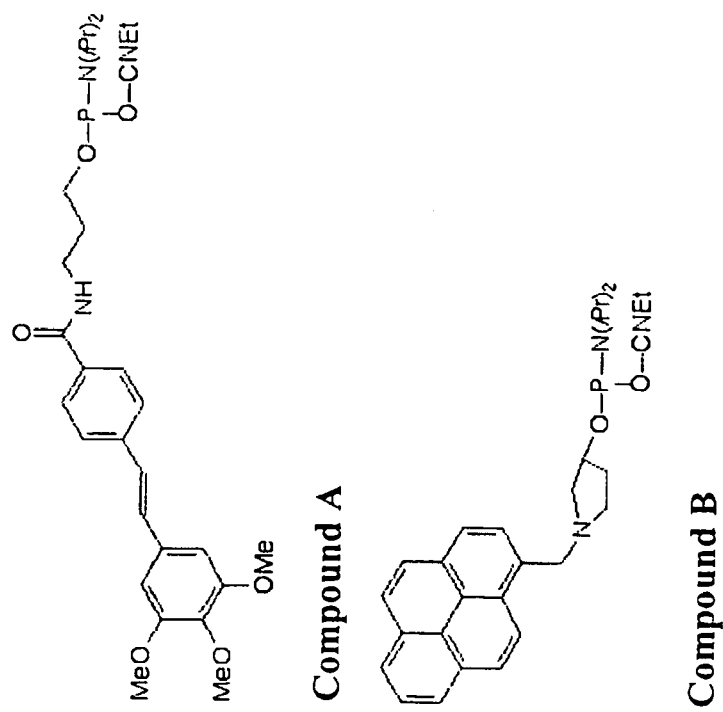
FIG. 14 shows the molecular structures of trimethoxystilbene and pyrenylmethylpyrrolindol two molecular caps that can be covalently bonded to the 5' end of partial strands in an iNA that have a nick or nucleotide gap.

Nucleotide Sequences of Constructs L3A & L3B Long Strand (SEQ ID NO: 39)
UCAGCGAUUUGAGAAAAUCGCUGAUUUGUGUAGdTdC L3A & 1L3B Short Sense Strand-CUACACAAA In the first 'U' of the long strands of constructs L3A and L3B, the nucleotide 5' position does not contain a phosphodiester bond forming a nick in the sense strands. A molecular cap, trimethoxystilbene, compound B in FIG. 14, is covalently bonded to the 'U' at the 5' end of the long strand of construct L3B. The last 'A' at the 3' end of the short strands of constructs L3A and L3B does not contain a phosphodiester bond forming a nick in the sense strand. The first 'C' at the 5' end of the short strand of the sense strand of construct L3B has a molecular cap, trimethoxystilbene, covalently bonded to the 'C'.

Nucleotide Sequence of Constructs L4A & L4B Long Strand (SEQ ID NO: 40)
GCGAUUUCCAUGUGAGAACAUGGAAAUCGCUGAUUUGUGUAGUC The first 'G' on the sense strand of the Long Strand of constructs L4A & L4B does not contain a phosphodiester bond at the 5' end of the nucleotide forming a nick in the sense strand. The first 'G' has on the sense long strand is covalently bonded at the 5' end to a molecular cap, trimethoxystilbene.

L4A & L4B Short Sense strand (SEQ ID NO: 41)
CUACACAAAUCA

The last 'A' on the 5' end of the short strands of constructs L4A & L4B does not contain a phosphodiester bond at the 3' end of nucleotide forming a nick in the sense strand. The first 'C' at the 5' end of the short strand of construct L4B has a molecular cap bonded to it.

Example 14

Inhibition of Lac Z Gene Using a 40 Mer iNA

Figure 16:
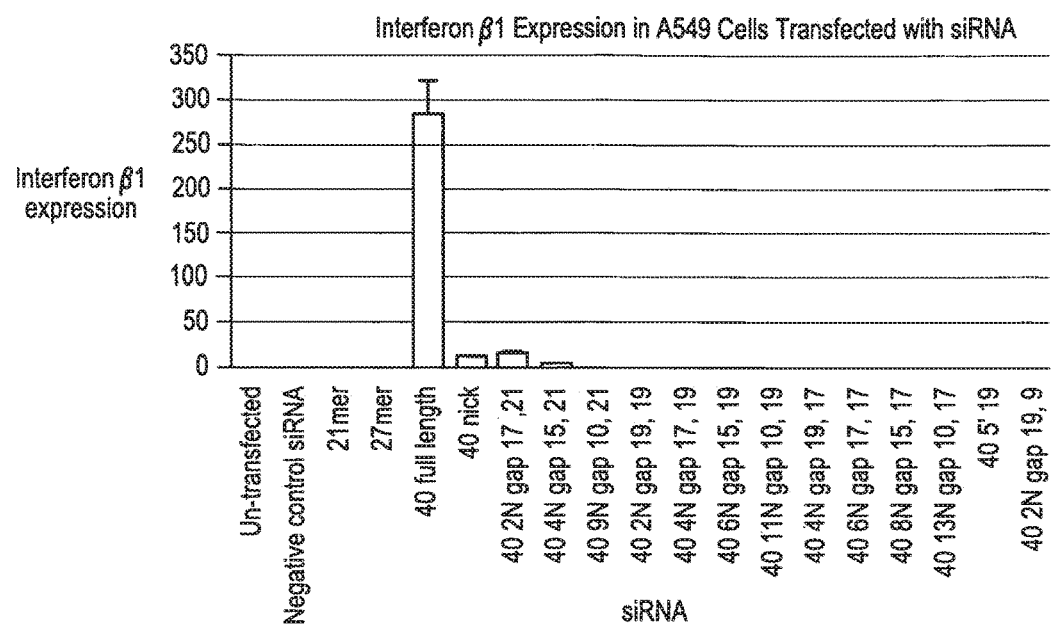
FIG. 16 shows the interferon response of 40 mer iNAs having nicks or gaps in the sense strand.
Figure 17:
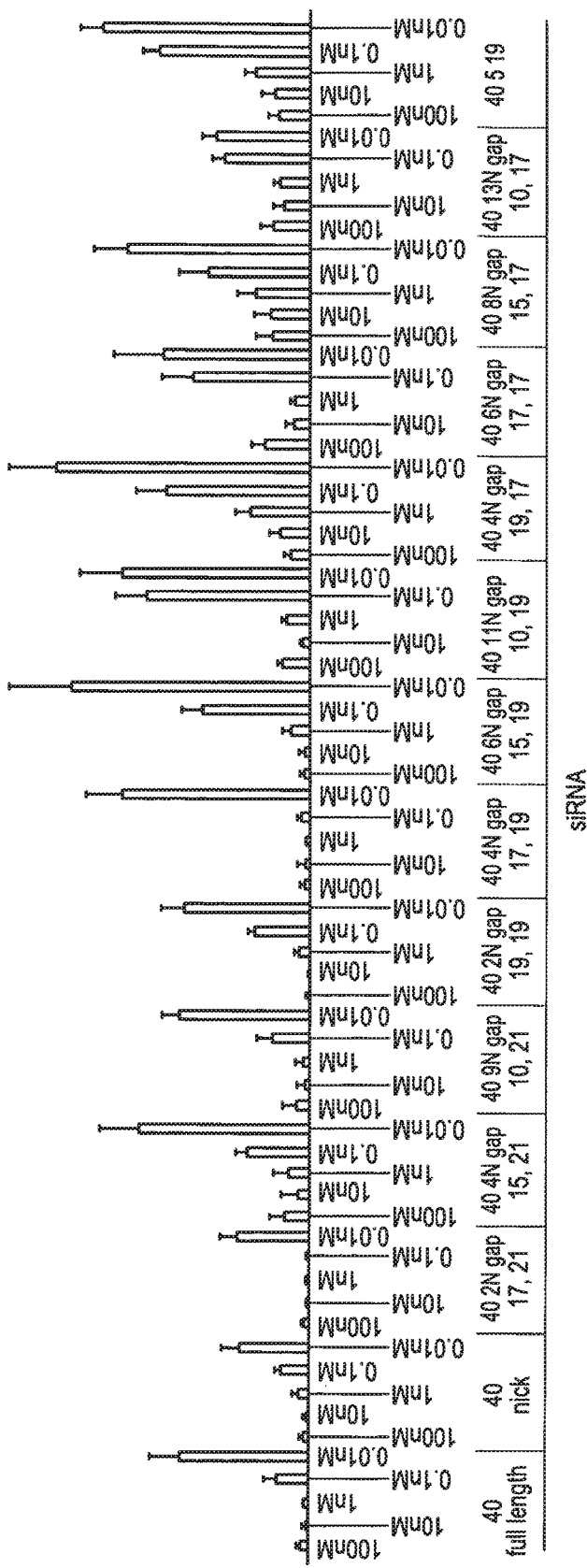
FIG. 17 shows the ability of 40 siRNAs with nicks or gaps in the sense strand to silence the Lac Z enzyme expression.
Figure 18:
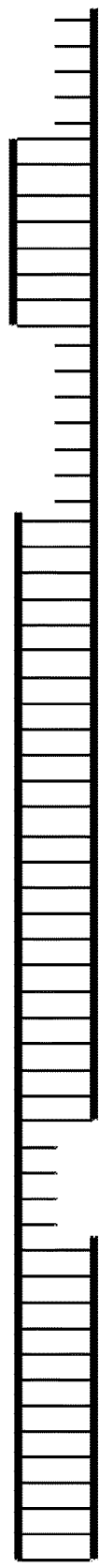
FIG. 18 shows an iNA construct of the present invention that has nucleotide gaps in the antisense and sense strands

Using the techniques described above a series of iNAs were designed targeting the LacZ gene, each iNA either having no gaps or nicks the sense or antisense strand or a series of nicks and gaps in the sense strand. FIGS. 16 and 17 show the results. The only construct that produced an appreciable interferon response, as shown in FIG. 16, was the iNA construct that had no nicks or gaps in either strand. While all of the iNA constructs were able to silence the LacZ gene.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

---

The invention claimed is:

1. An interfering nucleic acid (iNA) duplex comprised of a sense strand of nucleotides having a 5' end and a 3' end annealed onto an antisense strand of nucleotides having a 5' end and a 3' end wherein the antisense strand has at least two segments, wherein one segment of the antisense strand can target a first RNA and another segment of the antisense strand can target a second RNA, or one segment of the antisense strand can target a first portion of an RNA and another segment of the antisense strand can target a second non-contiguous portion of said RNA, wherein the sense strand or the antisense strand or both are discontinuous, and wherein the iNA does not induce an interferon-response when transfected into a cell.

2. The iNA duplex of claim 1, wherein there is a nick or gap between 2 nucleotides in the sense strand wherein said nucleotide gap in said sense strand is at least 1-20 nucleotides in length.

3. The iNA duplex of claim 2, wherein there is a nucleotide modification on one or more of the nucleotides on the sense strand and wherein the nucleotide modification is either a pyrrolindol or a stilbene linked to a nucleotide.

4. The iNA duplex of claim 3, wherein the pyrrolindol is pyrenylmethylpyrrolindol and the stilbene is trimethoxystilbene.

5. The iNA duplex of claim 1, wherein there is a nick between 2 nucleotides in the antisense strand or a nucleotide gap in the antisense strand wherein said nucleotide gap in said antisense strand is at least 1-20 nucleotides in length.

6. The iNA duplex of claim 5, wherein there is a nucleotide modification on one or more of the nucleotides on the antisense strand and wherein the nucleotide modification is either a pyrrolindol or a stilbene linked to a nucleotide.

7. The iNA duplex of claim 6, wherein the pyrrolindol is pyrenylmethylpyrrolindol and the stilbene is trimethoxystilbene.

8. The iNA duplex of claim 1, wherein the 3' end of the sense strand is connected to the 5' end of the antisense strand by means of a hairpin-loop of nucleotides.

9. The iNA duplex of claim 1, wherein the iNA duplex is at least 30-80 nucleotides in length.

10. The iNA duplex of claim 1, comprising a sense strand of nucleotides and two or more antisense strands annealed to the sense strand wherein there is at least one nucleotide gap or a nick between the antisense strands, and wherein the iNA duplex has a length of at least 30 nucleotides, and wherein each antisense strand a has 5' and a 3' end and the sense strand has a 5' end and a 3' end.

11. The iNA duplex of claim 10, wherein each antisense strand targets a different mRNA or mRNA.

12. The iNA duplex of claim 10, wherein each antisense strand targets different portions of an mRNA or miRNA.

13. The iNA duplex of claim 10, wherein the 5' end of the sense strand is connected to the 3' end of the antisense strand by means of a hairpin-loop of nucleotides.

14. The iNA duplex of claim 10, wherein the gap between the antisense strands is at least 1-20 nucleotides in length.

15. The iNA duplex of claim 10, wherein each antisense strand is at least 15 nucleotides in length.

16. The iNA duplex of claim 10, wherein there is a nucleotide gap or nick in the sense strand.

17. The iNA duplex of claim 1, wherein the antisense strand is annealed to the sense strand, wherein there is at least one nick or one nucleotide gap in the antisense strand, and wherein the iNA duplex has a length of at least 30 nucleotides and wherein there is at least one nick or at least one nucleotide gap in the sense strand.

18. The iNA duplex of claim 1, comprising two or more sense strands and two or more antisense strands wherein the antisense strands are annealed to the sense strands so as to produce one iNA duplex, and wherein said iNA duplex has a length of at least 30-80 nucleotides.

19. A pharmaceutical composition comprised of an iNA duplex having a sense strand of nucleotides having a 5' end and a 3' end annealed onto two or more antisense strands of nucleotides each strand having a 5' end and a 3' end wherein one antisense strand can target a first mRNA and one antisense strand can target a second mRNA, or one antisense strand can target one site on an mRNA and one antisense strand can target another non-contiguous site on said mRNA and wherein the iNA does not induce an interferon-response when transfected into a cell, and a pharmaceutically acceptable excipient.

20. The pharmaceutical composition of claim 19, wherein the first mRNA encodes a ligand and the second mRNA encodes a receptor to said ligand.

21. A method of down-regulating an mRNA in a mammal comprising administering the pharmaceutical composition of claim 19 to the mammal.

22. The iNA duplex of claim 2, wherein there is a nucleotide modification on one or more of the nucleotides on the sense strand and wherein the nucleotide modification is a pyrrolindol linked to a nucleotide.

23. The iNA duplex of claim 1, comprising a sense strand of nucleotides and two antisense strands annealed to the sense strand wherein there is at least one nucleotide gap or a nick between the antisense strands, and wherein the iNA duplex has a length of at least 30 nucleotides, and wherein each antisense strand a has 5' and a 3' end and the sense strand has a 5' end and a 3' end.

* * * * *